(12) United States Patent
Cohen

(10) Patent No.: US 10,071,185 B2
(45) Date of Patent: *Sep. 11, 2018

US010071185B2

(54) COMPARTMENTAL EXTRACT COMPOSITIONS FOR TISSUE ENGINEERING

(75) Inventor: Shahar Cohen, Kiryat Bialik (IL)

(73) Assignee: NAYACURE THERAPEUTICS LTD., Kiryat Bialik (IL)

( * ) Notice: Subject to any disclaimer, the term of this patent is extended or adjusted under 35 U.S.C. 154(b) by 13 days.

This patent is subject to a terminal disclaimer.

(21) Appl. No.: 12/866,627

(22) PCT Filed: Feb. 8, 2009

(86) PCT No.: PCT/IL2009/000147
§ 371 (c)(1),
(2), (4) Date: Sep. 14, 2010

(87) PCT Pub. No.: WO2009/098698
PCT Pub. Date: Aug. 13, 2009

(65) Prior Publication Data
US 2011/0008397 A1     Jan. 13, 2011

Related U.S. Application Data

(60) Provisional application No. 61/026,918, filed on Feb. 7, 2008, provisional application No. 61/026,938, filed on Feb. 7, 2008.

(51) Int. Cl.
| *A61K 9/00* | (2006.01) |
| *A61K 36/00* | (2006.01) |
| *A61K 35/12* | (2015.01) |
| *A61L 27/36* | (2006.01) |
| *A61L 27/38* | (2006.01) |
| *C12M 1/12* | (2006.01) |
| *C12M 1/42* | (2006.01) |
| *A61K 35/00* | (2006.01) |

(52) U.S. Cl.
CPC .......... *A61L 27/3604* (2013.01); *A61L 27/38* (2013.01); *C12M 25/14* (2013.01); *C12M 35/04* (2013.01); *A61K 35/00* (2013.01)

(58) Field of Classification Search
CPC ........ A61K 35/00; A61K 35/12; A61K 36/00; A61K 9/00; C12M 25/14
USPC ............... 424/400, 520, 725, 93.7; 435/536
See application file for complete search history.

(56) References Cited

U.S. PATENT DOCUMENTS

| 4,642,120 A | 2/1987 | Nevo et al. |
| 4,846,835 A | 7/1989 | Grande |
| 5,041,138 A | 8/1991 | Vacanti et al. |
| 5,514,378 A | 5/1996 | Mikos et al. |
| 5,618,718 A | 4/1997 | Auger et al. |
| 5,641,518 A | 6/1997 | Badylak et al. |
| 5,786,217 A | 7/1998 | Tubo et al. |
| 5,811,094 A | 9/1998 | Caplan et al. |
| 5,843,780 A | 12/1998 | Thomson |
| 5,855,620 A | 1/1999 | Bishopric et al. |
| 5,888,807 A | 3/1999 | Palsson et al. |
| 6,099,567 A | 8/2000 | Badylak et al. |
| 6,596,274 B1 | 7/2003 | Abatangelo et al. |
| 7,264,826 B2 | 9/2007 | Vervaet et al. |
| 8,076,137 B2 | 12/2011 | McAllister et al. |
| 8,778,416 B2 * | 7/2014 | Cohen ........................ 424/725 |
| 2004/0037813 A1 * | 2/2004 | Simpson .................. A61F 2/08 424/93.7 |
| 2004/0136968 A1 | 7/2004 | Zheng et al. |
| 2004/0241838 A1 | 12/2004 | Johnson et al. |
| 2006/0153797 A1 | 7/2006 | Bortolotto et al. |
| 2007/0225631 A1 | 9/2007 | Bowlin et al. |
| 2007/0292401 A1 | 12/2007 | Harmon et al. |
| 2008/0213389 A1 | 9/2008 | Lelkes et al. |
| 2008/0254092 A1 | 10/2008 | McDevitt et al. |
| 2008/0260831 A1 | 10/2008 | Badylak et al. |

FOREIGN PATENT DOCUMENTS

| WO | 9603093 | 2/1996 |
| WO | 9632905 | 10/1996 |
| WO | 9825636 | 6/1998 |
| WO | 02097065 | 12/2002 |

(Continued)

OTHER PUBLICATIONS

El-Sabban et al. Regen Med. Jul. 2007;2(4):383-90.*
International Search Report for PCT/IL2009/000147, Completed by the European Patent Office dated Mar. 3, 2010, 3 Pages.
Collas et al. Cloning and Stem Cells 2007, vol. 9, No. 1, p. 26-32, "Novel Approaches to Epigenetic Reprogramming of Somatic Cells."
Elsabban et al. Regen. Med. 2007, vol. 2, No. 4, p. 383-390, "Xenogenic bone matrix extracts induce osteoblastic differentiation of human bone marrow-derived mesenchymal stem cells."
Lavik et al. Appl Microbiol Biotechnol 2004, vol. 65, p. 1-8, "Tissue engineering: current state and perspectives."

(Continued)

*Primary Examiner* — Janet L Epps-Smith
(74) *Attorney, Agent, or Firm* — Browdy and Neimark, PLLC

(57) ABSTRACT

The present invention concerns biologically-active cell-free scaffolds composed of extracts of cellular and/or extracellular compartments for use in tissue regeneration. The present invention also contemplates the novel concept of redesigning the biological scaffold by seeding cells thereon followed by cell elimination. Cells are seeded on the scaffold for a period of time during which a dynamic interaction occurs between the scaffold and the seeded cells, resulting in reshaping of the scaffold architecture and integration of newly synthesized matrix elements. Redesigning may improve the physical and biological characteristics of the scaffold, and also improve the matching of the scaffold to treat a specific target tissue or a specific patient, by seeding tissue-specific cells or by seeding cells which are autologous to a patient, respectively.

22 Claims, 4 Drawing Sheets

(56) References Cited

FOREIGN PATENT DOCUMENTS

| WO | 03050266 | 6/2003 |
|---|---|---|
| WO | 2004029230 | 4/2004 |
| WO | 2005001079 | 1/2005 |
| WO | 2005002601 A1 | 1/2005 |
| WO | 2005121316 | 12/2005 |
| WO | 2006138718 | 12/2006 |
| WO | 2007005595 | 1/2007 |
| WO | 2007056547 | 5/2007 |
| WO | 2007149861 | 12/2007 |
| WO | 2008109407 | 9/2008 |

OTHER PUBLICATIONS

Nelson et al. Annu. Rev. Cell Dev. Biol. 2006, vol. 22, p. 287-309, "Of Extracellular Matrix, Scaffolds, and Signaling: Architecture Regulated Development, Homeostasis, and Cancer."

Sharma et al. Annals of Biomedical Engineering Jan. 2004, vol. 32, No. 1, p. 148-159, "Engineering Structurally Organized Cartilage and Bone Tissues."

Vacanti et al. The Lancet Jul. 1999, vol. 354, p. S32-S34, "Tissue engineering: The design and fabrication of living replacement devices for surgical reconstruction and transplantation."

\* cited by examiner

COMPARTMENTAL EXTRACT COMPOSITIONS FOR TISSUE ENGINEERING

This application claims the benefit of U.S. provisional application Ser. No. 61/026,918 filed Feb. 7, 2008 and 61/026,938 filed Feb. 7, 2008.

FIELD OF THE INVENTION

This invention relates to the field of tissue regeneration. More specifically, it describes the use of cell extracts to form scaffolds for tissue regeneration and the use of cells to redesign the scaffolds to achieve desired characteristics.

LIST OF REFERENCES

The following references are considered to be pertinent for the purpose of understanding the background of the present invention:
1. Vacanti, J. P. & Langer, R. Tissue engineering: the design and fabrication of living replacement devices for surgical reconstruction and transplantation. Lancet 354 Suppl 1, SI32-34 (1999).
2. Lavik, E. & Langer, R. Tissue engineering: current state and perspectives. Appl Microbiol Biotechnol 65, 1-8 (2004).
3. Sharma, B. & Elisseeff, J. H. Engineering structurally organized cartilage and bone tissues. Ann Biomed Eng 32, 148-159 (2004).
4. Collas, P. & Gammelsaeter, R. Novel approaches to epigenetic reprogramming of somatic cells. Cloning Stem Cells 9, 26-32 (2007).
5. Nelson, C. M. & Bissell, M. J. Of extracellular matrix, scaffolds, and signaling: tissue architecture regulates development, homeostasis, and cancer. Annu Rev Cell Dev Biol 22, 287-309 (2006).
6. U.S. Pat. No. 7,264,826
7. WO05/121316
8. WO 06/138718
9. WO 07/149,861

BACKGROUND OF THE INVENTION

Tissue engineering (TE) and regenerative medicine are evolving interdisciplinary fields based on both biological and engineering principles. These fields attempt to mimic the natural processes of tissue formation and regeneration (Vacanti and Lander, 1999). In a context of organ shortage, and an ever increasing number of patients on waiting lists for transplants, TE offers a viable alternative to the existing therapeutic options, as it promises to provide transplantable substitutes that restore, maintain or improve tissue function and integrity. Traumatic injury, tumor resections, degenerative disease, and congenital or acquired malformations can all require the reconstruction of adult tissue. Traditional approaches in reconstructive surgery, such as autografts, allografts or synthetic substitutes, are all inherently problematic. Autograft based therapy is limited by host morbidity and availability; allograft based therapy is limited by immune rejection and the risk of disease transmission; synthetic grafts are inferior to their biological counterparts, and have a relatively high failure rate.

TE is based on the use of cells, scaffolds and bioactive factors, such as chemical substances and mechanical stimuli. A number of cell types have already been used for TE applications, including fully matured cells derived from adult tissues, and stem cells. Stem cells can maintain and repair tissues, and can be derived from embryonic, fetal or adult sources (Lavik and Langer, 2004; Sharma and Elisseeff, 2004).

Nonetheless, several fundamental obstacles still need to be addressed when designing cell-based therapies, such as the risk of rejection of transplanted cells by the host immune system, and the risk of uncontrolled differentiation and proliferation of the transplanted cells, which can result in tumor formation.

While autologous cell-based strategies may offer a solution to immune rejection problems, patient-specific therapies raise critical questions regarding regulatory and economic issues.

It has also been shown that an extract from pluripotent cells, such as oocytes and embryonic stem cells, can manipulate gene expression and epigenetically reprogram somatic cells (Collas and Gammelsaeter 2007). In addition, the extracellular microenvironment is also known to play a significant role in modulating cell phenotype and behavior (Nelson and Bissell 2006).

U.S. Pat. No. 7,264,826 discloses pharmaceutical compositions comprising keratinocyte cell lysate and at least one antiflocculant and/or antisedimentation agent for treating skin wounds.

WO 2007/149861 discloses pharmaceutical compositions comprising stem cell products (SCP), e.g. cell fractions or cell lysates. This application also discloses a matrix combined with SCPs for administration to a patient, as well as methods of regenerating soft tissue in a patient comprising administering the stem cell compositions or the matrices.

WO 06/138718 discloses a biologically active three-dimensional scaffold which can be obtained from non-structural ECM extracts. The invention employs MATRIGEL which is a complex mixture of non-structural ECM molecules (such as collagen IV and laminin) and further contains growth factors and other biologically active molecules.

WO05/121316 discloses tissue-based scaffolds for supporting the growth, development and differentiation of cells and for supporting or effecting morphological changes to cells. The tissue material is preferably derived from muscle tissue and comprises a preparation comprising basement membrane components.

SUMMARY OF THE INVENTION

The present invention is based on the understanding that the cellular components of cells can serve as a rich source of factors such as growth factors, cytokines, structural elements and transcription factors which are important to direct regeneration of adult tissue. Accordingly, the present invention provides scaffold formulations that are composed of various intracellular extracts or extracellular extracts for use in regenerative medicine.

By a first of its aspects, the present invention provides a scaffold composed of a cell extract.

In accordance with the invention, the cell extract is prepared from a cell selected from the group consisting of: a primary cell, a cultured cell, or a cell line. The cell extract can also be prepared from an engineered tissue, or from a primary tissue.

In certain embodiments the cell extract is prepared from a cell selected from the group consisting of epithelial cell, neural cell, epidermal cell, keratinocyte, hematopoietic cell, melanocyte, chondrocyte, hepatocyte, B-cell, T-cell, erythrocyte, macrophage, monocyte, fibroblast, muscle cell, vascular smooth muscle cell, and a stem cell. The cell extract may also be prepared from a plant cell.

In accordance with the invention said stem cell is selected from a group consisting of undifferentiated stem cell, pluripotent stem cell, lineage-restricted stem cell, precursor cell, somatic stem cell, terminally differentiated somatic stem cell, cells expressing one or more markers of multilineage differentiation potential, cells expressing one or more markers of pluripotent stem cells, hematopoietic stem cells, neural stem cells, mesenchymal stem cells, embryonic germ cells, and embryonic stem cells.

In one embodiment, said cell extract is prepared from a mammalian cell. In a specific embodiment, said mammalian cell is a human cell.

In certain embodiments the cell extract is selected from the group consisting of a cytosolic extract, a cytoplasmic extract, a nuclear extract, a whole cell lysate, extracellular extract, whole tissue extract and mixtures thereof.

In a specific embodiment, the scaffold of the invention is prepared from a cell which is cultured in a cell culture device capable of exerting mechanical forces onto the cultured cells and is having a patterned surface.

In an embodiment, the scaffold of the invention is suitable for administration to a mammal for use in conditions necessitating tissue or organ regeneration, repair or replacement. Such conditions in accordance with the invention are selected from the group consisting of: cardiovascular surgery, plastic surgery, wound healing, soft tissue reconstruction, orthopedics, dental surgery, gastrointestinal surgery, thoracic surgery, urology, gynecology, neurological conditions, endocrine deficiencies, skeletal deficiencies, autoimmune disorders, and hematopoeitic deficiencies.

In a specific embodiment the scaffold of the invention further comprises a scaffold-enhancing agent.

In accordance with certain embodiments the scaffold is a cell-free scaffold.

In another embodiment the scaffold is seeded with cells prior to administration. In a specific embodiment, the seeded cells are eliminated from the scaffold prior to administration.

The interaction of the seeded cells with the scaffold results in redesigning of the scaffold. Redesigning may consist of one or more cycles of cell seeding and elimination, wherein one or more cell types are seeded onto the scaffold simultaneously or sequentially.

The invention also provides use of the scaffold for preparing an injectable scaffold formulation.

In one embodiment the preparation comprises solubilizing said scaffold.

In another aspect, the present invention provides use of a cell extract for preparing a scaffold for use in conditions necessitating tissue or organ regeneration, repair or replacement.

In another aspect, the present invention provides a method of preparing a scaffold for use in conditions necessitating tissue or organ regeneration, repair or replacement, comprising:
 (a) Obtaining cells or tissues;
 (b) Preparing a cell or a tissue extract;
 (c) Preparing a scaffold from said cell extract.

In a specific embodiment, the scaffold preparation in step (c) is performed by electrospinning.

In another aspect, the present invention provides a method for producing a scaffold, comprising:
 (a) Obtaining cells or tissues;
 (b) Preparing extracellular extracts and/or intracellular extracts from said cells or tissues;
 (c) Preparing a scaffold from said extracellular or intracellular extracts;
 (d) Redesigning said scaffolds by seeding cells thereon;
 (e) Eliminating the cells from the scaffold; and either
 (f) Administering the scaffold into a host in need thereof, or solubilizing the scaffold, thereby obtaining an injectable scaffold formulation.

In certain embodiments, said intracellular extracts are prepared from separate cellular compartments, selected from a group consisting of a cytosolic compartment, a cytoplasmic compartment, a nuclear compartment, and any combination thereof.

In a specific embodiment, said cells or tissues are cultured in a cell culture device capable of exerting mechanical forces onto the cultured cells and is having a patterned surface, prior to step (b).

In another specific embodiment, said cell seeding onto said scaffold in step (d) is performed in a cell culture device capable of exerting mechanical forces onto the cultured cells and is having a patterned surface.

In one embodiment, said extracellular and/or intracellular extracts are further combined with a tissue extract.

In another aspect, the present invention provides a method of providing support to a tissue by administering the scaffold of the invention in proximity to said tissue.

In another aspect, the present invention provides a method of treating conditions necessitating tissue or organ regeneration, repair or replacement in a patient comprising administering to the patient the scaffold of the invention.

In another aspect, the present invention provides a cell culture device for culturing cells and producing extracellular matrix components, wherein said cells and extracellular matrix components are further used for fabricating a scaffold, and wherein said cell culture device is capable of exerting mechanical forces onto the cultured cells and is having a patterned surface.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1A:
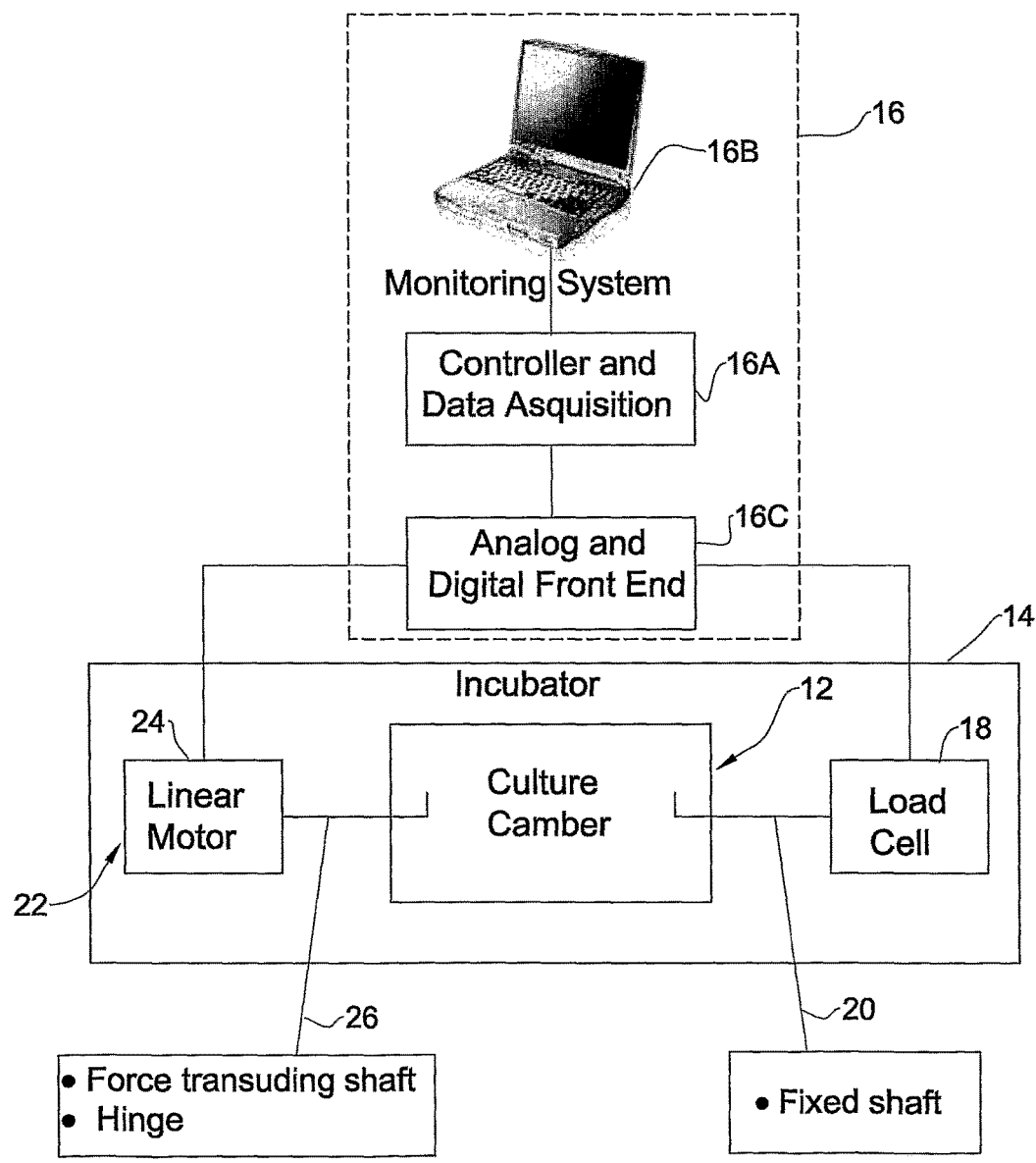
FIG. 1 is a schematic representation of a cell culture device.

The present invention is based on the understanding that the cellular components of cells can serve as a rich source of factors such as growth factors, cytokines, structural elements and transcription factors which are important to direct regeneration of adult tissue. Particularly, the cellular components of stem cells have the potential to elicit reprogramming events in mature cells and direct regeneration of adult tissue.

It is well known that multiple processes involving the sequential expression of various proteins are necessary for optimal tissue repair and remolding. Based on this concept, optimal tissue cannot be achieved by the administration of a single bioactive factor. Because of the complexity of tissue restoration processes, various factors such as growth factors, and cytokines involved in tissue restoration may be required for optimal repair.

Accordingly, the present invention concerns biologically-active cell-free scaffolds composed of cellular components for use in tissue regeneration. Using a cell-free scaffold for regenerative medicine instead of a cell-based construct could dramatically decrease the risks associated with cell therapy, e.g. tumor formation and immune rejection, essentially enabling the design of "off the shelf" technology for allogeneic use.

Therefore, methods for engineering cell-free biological scaffolds composed of cell extracts which are capable of regenerating adult tissues are highly desirable. Such cell-free constructs can serve as an alternative to cell-based therapies.

In principal, the biological scaffolds of the invention can be used as a cell-free preparation although in certain embodiments the scaffold may be seeded with desired cells prior to transplantation into the host.

The present invention also contemplates the novel concept of redesigning the scaffold by seeding cells thereon followed by cell elimination. Cells are seeded on the scaffold for a period of time during which a dynamic interaction occurs between the scaffold and the seeded cells, resulting in redesigning of the scaffold. Redesigning includes for example global reshaping of the scaffold architecture and integration of newly synthesized matrix elements. Redesigning may improve the physical and biological characteristics of the scaffold, and also improve the matching of the scaffold to treat a specific target tissue or a specific patient, by seeding tissue-specific cells or by seeding cells which are autologous to a patient, respectively. In a specific embodiment the cell-free scaffold is obtained from a stem cell extract and thus induces reprogramming of the seeded cells into desired cell types.

In certain embodiments, redesigning is performed serially by seeding different types of cells in a consecutive manner, or simultaneously by seeding a mixed population of several types of cells. Cell seeding for redesigning the scaffold is followed by cell elimination, which may be achieved by any suitable technique.

The scaffold of the invention can be provided as an injectable scaffold and/or as a transplantable scaffold as further detailed below.

Such biological scaffolds stimulate tissue regeneration by providing regulatory factors, such as cytokines, growth factors and transcription factors and thereby enable host cells to migrate, proliferate and differentiate thereon.

In one of its aspects, the present invention provides use of cellular components (for example in the form of cell extracts) to construct cell-free biological scaffolds for tissue regeneration.

In another aspect, the present invention provides methods for preparing biological scaffolds composed of cell-free extracts of cells containing regulatory factors, such as cytokines, growth factors and transcription factors from various kinds of cells and tissues.

In particular embodiments said cell extracts are obtained from stem cells.

The scaffolds of the present invention are provided for reconstruction, repair, augmentation or replacement of tissue and organs in a patient in a need thereof. Other usages of the scaffolds are provided as well.

The biologically active scaffolds of the invention may be used in various fields of regenerative medicine, including, but not limited to, cardiovascular surgery, plastic surgery, wound healing, soft tissue reconstruction, orthopedics, dental surgery, gastrointestinal surgery, thoracic surgery, urology, gynecology, neurological conditions, endocrine deficiencies, skeletal deficiencies, autoimmune disorders, and hematopoeitic deficiencies.

The biologically active scaffolds of the invention are also suitable for veterinary use, namely in organ/tissue regeneration of animal injuries. As a non limiting example, the scaffolds of the invention may be used for reconstruction or reinforcement of injured tendons and other skeletal tissues in horses and dogs.

In one embodiment, the cell extract comprises the intracellular compartment of pluripotent stem cells. The pluripotent stem cells are preferably undifferentiated. Furthermore, the pluripotent stem cells are preferably of mammalian origin, more preferably of human origin.

The cell extracts may be obtained from primary cells, cell lines, cultured cells, primary tissue or engineered tissue prepared in vitro. The cultured cells can be cultured in standard culture plates or in a cell culture device capable of exerting mechanical forces onto the cultured cells and having a patterned surface. Such a device is capable of directing cell orientation and inducing mechanical stimulation thereon.

In yet another aspect, the present invention provides a cell culture device for culturing cells and producing intra- and extra-cellular matrix components, wherein said cells and extracellular matrix components are further used for the fabrication of a scaffold, and wherein said cell culture device is capable of exerting mechanical forces onto the cultured cells and having a patterned surface.

Without wishing to be bound by theory, the culture device provides an environment for cell growth which mimics the natural environment of cells and tissues, i.e. the animal body. The combination of mechanical stimulation and a nano-scale or micro-scale patterned topography has a significant effect on the organization, orientation, growth, maturation and function of cells and tissues, e.g. enhanced amounts of ECM is produced, the cell fibers are stronger, the transcriptional activity and other intra- and extracellular activities are potentiated, and enhanced levels of various cytokines, and growth factors are produced thereby serving as a richer source for scaffold preparation.

In a specific embodiment, the present invention provides a method for producing a biologically active scaffold, comprising:
  (a) Obtaining cells or tissues; optionally culturing the cells prior to further use;
  (b) Preparing extracellular extracts and intracellular extracts from said cells or tissues; optionally said cellular extracts are prepared from separate cellular compartments, e.g. cytosolic fraction, cytoplasmic fraction or nuclear fraction;
  (e) Preparing a scaffold from said extracellular or cellular extracts, for example by using electrospinning;
  (d) Redesigning said scaffolds by seeding cells thereon, and allowing said cells to interact in a molecular, structural and functional way with the scaffold, e.g. to reshape the scaffold architecture and to integrate newly synthesized matrix elements;
  (e) Eliminating the cells from the scaffold; and either
  (f) Administering the scaffold into a host in need thereof, or solubilizing the scaffold thereby obtaining an injectable scaffold formulation.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art e.g., Sambrook and Russell, 2001, Molecular Cloning, A Laboratory Approach, Cold Spring Harbor Laboratory Press, Cold Spring Harbor, N.Y.; and Ausubel et al., 2002, Current Protocols in Molecular Biology, John Wiley & Sons, New York, N.Y.

The articles "a" and "an" are used herein to refer to one or to more than one (i.e., to at least one) of the grammatical object of the article. By way of example, "an element" means one element or more than one element.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, "administering" refers to the application of biological scaffolds to a subject. Administration includes any means for applying the scaffold to a patient, including but not limited to implantation, topical application and injection.

The term "attached" as used herein encompasses interaction including, but not limited to, covalent bonding, ionic bonding, and mechanical interactions.

The term "biomolecule" refers to an organic molecule typically made by living organisms. This includes, for example, nucleotides, amino acids, sugars, fatty acids, steroids, nucleic acids, polypeptides, peptides, peptide fragments, carbohydrates, lipids, and combinations thereof (e.g., glycoproteins, ribonucleoproteins, lipoproteins, and the like).

The term "differentiation factor" or "differentiation agent" as used herein, refers to a molecule that induces a stem cell or a progenitor cell to commit to a particular specialized cell type.

"Extracellular matrix" ("ECM") refers to one or more substances that line the extracellular space around cells in vivo or in culture and support cell growth. Components of an extracellular matrix can include for example laminin, collagen, fibronectin and elastin.

The term "electroprocessing" shall be defined broadly to include all methods of electrospinning, electrospraying, electroaerosoling, and electro sputtering of materials, combinations of two or more such methods, and any other method wherein materials are streamed, sprayed, sputtered or dripped across an electric field and toward a target. The electroprocessed material can be electroprocessed from one or more grounded reservoirs in the direction of a charged substrate or from charged reservoirs toward a grounded target. The term electroprocessing is not limited to the specific examples set forth herein, and it includes any means of using an electrical field for depositing a material on a target.

As used herein, the term "electrospinning" also known as "electrostatic spinning," includes various processes for forming polymeric fibers including nanofibers and microfibers by expressing a liquid polymeric formulation through a capillary, syringe or similar implement (referred to herein as a flow tube) under the influence of an electrostatic field and collecting the so-formed fibers on a target.

"Growth factor" refers to a substance that is effective to promote the growth of cells. For example, basic fibroblast growth factor (bFGF), acidic fibroblast growth factor (aFGF), epidermal growth factor (EGF), insulin-like growth factor I (IGF-I), insulin-like growth factor-II (IGF-II), platelet-derived growth factor (PDGF), vascular endothelial growth factor (VEGF), bone morphogenic proteins (BMPs), insulin, cytokines, chemokines, morphogens.

"Hydrogel" refers to a water-insoluble and water-swellable cross-linked polymer that is capable of absorbing at least 3 times, preferably at least 10 times, its own weight of a liquid. "Hydrogel" can also refer to a "thermo-responsive polymer" as used herein.

As used herein, "scaffold" and "matrix" are used interchangeably and refer to a structure, comprising a biocompatible material that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

A "biologically active scaffold" as used herein, refers to a scaffold which serves as an infrastructure for cell growth and provides biologically active agents to the tissue or organ into which it was implanted.

The term "isolated" refers to a material that is substantially or essentially free from components, which are used to produce the material. The lower end of the range of purity for the compositions is about 60%, about 70% or about 80% and the upper end of the range of purity is about 70%, about 80%, about 90% or more than about 90%. The term isolate can be used with reference to cells, polypeptides nucleic acids etc. Accordingly, an "isolated cell" refers to a cell which has been separated from other components and/or cells which naturally accompany the isolated cell in a tissue or mammal.

As used herein, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein the term "injectable" refers to a form of a scaffold that is non-solid. It encompasses, but is not limited to, a gel, a suspension or a solution, as well as a powder form amenable for rehydration.

As used herein "mammal" includes embryonic, juvenile, and adult mammals, unless the context clearly indicates otherwise. Mammals include, for example, humans, cows, sheep, big-horn sheep, goats, buffalos, antelopes, oxen, horses, donkeys, mule, deer, elk, caribou, water buffalo, camels, llama, alpaca, rabbits, pigs, mice, rats, guinea pigs, hamsters, dogs, cats, and primates such as monkeys.

As used herein, a "graft" refers to a cell, tissue or organ that is implanted into an individual, typically to replace, correct or otherwise overcome a defect. A graft may further comprise a scaffold. The tissue or organ may consist of cells that originate from the same individual; this graft is referred to herein by the following interchangeable terms: "autograft", "autologous transplant", "autologous implant" and "autologous graft". A graft comprising cells from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

As used herein, the terms "treat", "treating" or "treatment" refers to the administration of therapy to an individual in an attempt to reduce the frequency and/or severity of symptoms of a disease, defect, disorder, or adverse condition of a patient.

As used herein, the terms "prevent", "preventing" and "prevention" refer to the administration of therapy to an individual who may ultimately manifest at least one symptom of a disease, disorder, or condition, but who has not yet done so, to reduce the chance that the individual will develop the symptom of the disease, disorder, or condition over a given period of time. Such a reduction may be reflected, for example, in a delayed onset of the at least one symptom of the disease, disorder, or condition in the patient.

"Proliferation" is used herein to refer to the reproduction or multiplication of similar forms, especially of cells. That is, proliferation encompasses production of a greater number of cells, and can be measured by, among other things, counting the number of cells, measuring incorporation of —H-thymidine into the cell, and the like.

"Tissue engineering" refers to the process of generating tissues ex vivo for use in tissue replacement or reconstruction. Tissue engineering is an example of "regenerative medicine" which encompasses approaches to the repair or replacement of tissues and organs by incorporation of cells, genes or other biological building blocks, along with bioengineered materials and technologies.

As used herein "endogenous" refers to any material from or produced inside an organism, cell or system.

"Exogenous" refers to any material introduced into or produced outside an organism, cell, or system.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "promoter" means a nucleic acid sequence which is required for expression of a gene product operably linked to the promoter. In some instances, this sequence may be the core promoter sequence and in other instances, this sequence may also include an enhancer sequence and other regulatory elements which are required for expression of the gene product. The promoter may, for example, be one which expresses the gene product in a tissue specific manner.

A "vector" is an agent which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acids into cells, such as, for example, polylysine compounds, liposomes, and the like. Examples of viral vectors include, but are not limited to, adenoviral vectors, adeno-associated virus vectors, retroviral vectors, and the like.

The term "patient" as used herein includes human and veterinary subjects.

As used herein, "wound healing" is intended to include all disorders characterized by any disease, disorder, syndrome, anomaly, pathology, or abnormal condition of the skin and/or underlying connective tissue, e.g., skin wounds following surgery, skin abrasions caused my mechanical trauma, caustic agents or burns, cornea following cataract surgery or corneal transplants, mucosal epithelium, wounds following infection or drug therapy (e.g., respiratory, gastrointestinal, genitourinary, mammary, oral cavity, ocular tissue, liver and kidney), diabetic wounds, skin wounds following grafting, and regrowth of blood vessels following angioplasty.

As used herein, a "stem cell" is a cell with the developmental potential to produce a more specialized cell type and at the same time to replicate itself. A stem cell may divide to produce two daughters that are themselves stem cells or it may divide to produce a daughter that is a stem cell and a daughter that is a more specialized cell type. A stem cell may originate from the embryo, fetus, or adult.

A "progenitor cell" or "precursor cell" is a cell which occurs in fetal or adult tissues and is partially specialized. It divides and gives rise to differentiated cells.

As used herein, a "pluripotent stem cell" is a stem cell with the developmental potential to produce ectodermal cell types, mesodermal cell types, and endodermal cell types.

An "embryonic stem cell" is a type of totipotent stem cell. That is, it is a cell that can give rise to every cell type in a mammal. A totipotent stem cell is a type of "pluripotent stem cell".

A "differentiated cell" is any cell with less developmental potential than a pluripotent stem cell.

As used herein, a "lineage-restricted stem cell" is a stem cell that can only give rise to cell types within one germ layer (i.e., to cell types within ectoderm or mesoderm or endoderm lineages). The lineage-restricted stem cell may have the potential to give rise to all cell types within the germ layer or it may only have the potential to give rise to a subset of cell types within the germ layer.

As used herein, a "pluripotent stem cell marker" is an mRNA or protein that is present in a pluripotent stem cell but absent in a lineage-restricted stem cell.

A "somatic stem cell" is a stem cell found in or isolated from a differentiated tissue, which can renew itself and give rise to at least one specialized cell type of the germ layer from which it originated. Non-limiting examples of somatic stem cells include "hematopoietic stem cells", "bone marrow stromal stem cells", "neural stem cells", "epithelial stem cells", and "skin stem cells". "Hematopoietic stem cells" give rise to all the types of blood cells: red blood cells, B lymphocytes, T lymphocytes, natural killer cells, neutrophils, basophils, eosinophils, monocytes, macrophages, and platelets. "Bone marrow stromal stem cells" give rise to a variety of cell types: bone cells (osteocytes), cartilage cells (chondrocytes), fat cells (adipocytes), and other kinds of connective tissue cells such as those in tendons. "Neural stem cells" in the brain give rise to its three major cell types: nerve cells (neurons) and two categories of non-neuronal cells—astrocytes and oligodendrocytes. "Epithelial stem cells" in the lining of the digestive tract occur in deep crypts and give rise to several cell types: absorptive cells, goblet cells, Paneth cells, and enteroendocrine cells. "Skin stem cells" occur in the basal layer of the epidermis and at the base of hair follicles. The epidermal stem cells give rise to keratinocytes, which migrate to the surface of the skin and form a protective layer. The follicular stem cells can give rise to both the hair follicle and to the epidermis.

A "somatic cell" is defined herein as a diploid cell of any tissue type that does not contribute to the propagation of the genome beyond the current generation of the organism. All cells except for germ cells are somatic cells and constitute the individual's body.

As used herein, the term "nuclear factor(s)" refers to proteins (or RNAs) normally bound within the nuclear membrane (except during mitosis in somatic cells and meiosis in germ cells). Nuclear factors may also include heteronuclear RNA ("hnRNA", i.e. messenger RNA prior to processing and export). The hnRNA may encode reprogramming factors. The nuclear factors may include DNA binding proteins bound in chromatin to the chromosomes, for example histones, transcription factors and other ancillary factors that may affect gene expression (either directly or indirectly).

"Reprogramming" is defined as a process by which a specific functional phenotype of a differentiated cell is expunged to yield a cell with a different functional phenotype.

The terms "cell culture" and "culture" encompass the maintenance of cells in an artificial, in vitro environment. It is to be understood, however, that the term "cell culture" is a generic term and may be used to encompass the cultivation not only of individual cells, but also of tissues, organs, organ systems or whole organisms, for which the term "tissue culture" may occasionally be used interchangeably with the term "cell culture."

The terms "cell culture medium" or "culture medium" (plural "media" in each case) refer to a nutritive solution for cultivating cells and may be used interchangeably.

The term "ingredient" refers to any compound, whether of chemical or biological origin, that can be used in cell culture media to maintain or promote the growth or proliferation of cells. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

I. Tissues

Cells for use in accordance with the present invention may be isolated from various types of organs or tissues, and are not limited to any particular species or type of tissue, organ or cell. Cell can be obtained or recovered from prenatal tissues, postnatal tissues, and adult tissues. Preferably, cells are isolated from human organs or tissues.

Non limiting examples of tissues encompassed by the present invention are: prenatal tissues, postnatal tissues, and adult tissues, obtained for example from: skin (as a source, for example, of dermal fibroblasts, muscle, blood, blood vessels, bone, fat, bone-marrow, dental pulp, nervous tissue, cartilage, tendons, ligaments, placenta, or umbilical cord blood. Discarded tissues may also be used in accordance with the present invention, for example, foreskins and tissue obtained during esthetic or cosmetic surgical procedures.

The various types of tissue samples can be obtained for example from a biopsy including but not limited to a needle biopsy, a small wedge biopsy, lipoaspiration, or a partial/complete, excision/resection of organs, a cadaver (a deceased donor), or from disposed organ tissue e.g. an aborted fetus.

For example, skeletal muscle biopsies can be obtained easily from the arm, forearm, or lower extremities, and smooth muscle biopsies can be obtained from the area adjacent to the subcutaneous tissue throughout the body.

The biopsy can be readily obtained with the use of a biopsy needle, a rapid action needle which makes the procedure extremely simple and almost painless.

The cells may be derived from the same organ as the intended target organ of the biological scaffold (e.g., derived from cardiovascular tissue for development of a vascular graft).

Cells may be obtained directly from the tissue or may be cultivated in culture prior to preparing an extract.

In one embodiment, the tissue or organ is cryopreserved and thawed prior to cell isolation and extract preparation.

Techniques for treatment of an organ or tissue to obtain cells are known to those skilled in the art (see, e.g. Freshney, Culture of Animal Cells. A Manual of Basic Technique, 2d Ed. A. R. Liss, Inc. New York, 1987, Ch. 9, pp. 107-126).

For example, the tissue or organ can be mechanically disrupted and/or treated with digestive enzymes or chelating agents to weaken the interactions between cells making it possible to obtain a suspension of individual cells.

Typically the method will include a combination of mechanical disruption, enzyme treatment and chelating agents. In one technique the tissue or organ is minced and treated simultaneously or subsequently with any of a number of digestive enzymes either alone or in combination.

Examples of enzymes useful in dissociating cells include, but are not limited to, trypsin, chymotrypsin, collagenase, elastase, hyaluronidase, DNase, pronase, dispase, liberase and the like. Mechanical disruption can also be accomplished by, for example, the use of blenders, sieves, homogenizers, pressure cells, and the like.

One specific method of isolating stromal cells (e.g., fibroblasts) includes the mincing of a tissue in Hank's Balanced Salt Solution (MSS) or other similar solution. The tissue is then incubated in a solution of trypsin under conditions and for a time sufficient to separate the cells (e.g. at about 4° C. for 1 to 12 hours). The separated cells are typically suspended in a high protein medium (e.g., media with fetal bovine serum or human serum (including autologous serum)), pelleted by centrifugation and plated onto tissue culture plates. Fibroblasts, for example, typically attach to the tissue culture plastic before other cells, thereby giving rise to a population of fibroblast cells. The resulting population of fibroblasts cells are typically substantially homogenous, but may contain additional cell types including macrophages, endothelial cells, epithelial cells, and the like, present in the tissue from which the fibroblasts are isolated.

It is preferable to use mechanical disruption of the tissue through microsurgical/homogenization procedures well known in the art followed by enzymatic dispersion using collagenase at a concentration of 0.5 to 5 mg/ml, most preferably at 0.5 mg/ml, in suitable buffer such as phosphate-buffered saline either with or without added calcium, magnesium or EDTA. A most preferable embodiment involves mechanical disruption into tissue fragments that are at least 1 mm³ in size followed by digestion in 0.5 mg/ml collagenase in PBS containing 1 raM EDTA, pH 7.2 to pH 7.5 at 37° C. for about 30 minutes. Other variations of this general method will be apparent to those skilled in the art and the present invention is not limited by the specific procedures used to generate dispersed tissue. Following enzymatic disruption, the enzymes used to prepare the dispersed tissue are washed out using a suitable solution such as phosphate-buffered saline followed by centrifugation by methods readily apparent to those skilled in the art.

As another example, the dermal layer of a skin biopsy can be digested with collagenase. After the digestion of the dermal fragments, mesenchymal cells are harvested following centrifugation and expanded in cell culture media.

The resulting suspension of cells and cell clusters can be further divided into populations of substantially homogenous cell types. This can be accomplished using standard techniques for cell separation including, for example, positive selection methods (e.g., clonal expansion and selection of specific cell types based on expression of specific cell surface markers), negative selection (e.g., lysis of unwanted cells), use of specific cell culture conditions, separation based upon specific gravity in a density solution (in density gradient centrifugation), differential adherence properties of the cells in the mixed population (differential adsorption), fluorescence activated cell sorting (FACS), immunomagnetic-based separation methods, and the like. Other methods of selection and separation are known in the art (see, e.g., Freshney, Culture of Animal Cells. A Manual of Basic Techniques, 2d Ed., A. R. Liss, Inc. New York, 1987, Ch. 11 and 12, pp. 137-168). Cells obtained by these methods are further expanded in culture using standard cell culture techniques known to those skilled in the art to obtain sufficient cell numbers as required for extract preparation.

Cell fractionation may be desirable, for example, when the donor has diseases such as cancer. A cell population may be sorted to separate malignant cells from normal noncancerous cells. The normal noncancerous cells, isolated using one or more of the sorting techniques, may then be used for cell component extraction.

The tissue/organ is generally handled using standard sterile techniques preferably in a laminar flow safety cabinet. In the use and processing of all human tissue, the recommendations of the U.S. Department of Health and Human Services/Centers for Disease Control and Prevention should be followed (Biosafety in Microbiological and Biomedical Laboratories, Richmond, J. Y. et al., Eds., U.S. Government Printing Office, Washington, D.C. 3rd Edition (1993)). Preferably, the tissue is collected in a medium with antibiotics and antimycotic drugs and transported in ice. The tissue is cut into small pieces (e.g., 0.1×0.1 mm) using sterile surgical instruments.

Cells may also be isolated from samples of animal tissue obtained via biopsy, autopsy, donation, or other surgical or medical procedure.

II. Cells

In accordance with the invention, the cells may be autologous, allogeneic or xenogeneic with respect to the host into which the scaffold is implanted.

The cells of the invention can be obtained from any type of animal. In one embodiment, cells are isolated from a mammal. In a preferred embodiment the cells are human cells. The cell extract may also be prepared from a plant cell.

The cell may be any cell type, including, for example, a differentiated cell, a precursor cell, or a stem cell. Some non-limiting examples include an epithelial cell (including oral and gastrointestinal mucosal epithelia, urinary tract epithelia), endothelial cell, vascular endothelial cell, neural cell, epidermal cell, keratinocyte, melanocyte, osteoblast, intervertebral disc cell, chondrocyte, hepatocyte, pancreatic cell, hematopoietic cell, angioblast, B-cell, T-cell, erythrocyte, macrophage, monocyte, bone marrow mesenchymal cell, fibroblast, myoblast, muscle cell, cardiomyocyte, amniotic or placental cell, or stem cell. The invention also contemplates use of cells of established cell lines, for example, HeLa cells, FL cells, KB cells, HepG2 cells, WI-88 cells, MA104 cells, BSC-1 cells, Vero cells, CV-1 cells, BHK-21 cells, L cells, CHL cells, BAE cells, BRL cells, PAE cells, as well as genetically engineered cells.

The cell may be a stem cell. Types of stem cells include: undifferentiated stem cells, pluripotent stem cells, lineage-restricted stem cells, precursor cells, somatic stem cells, terminally differentiated somatic stem cells, cells expressing one or more markers of multilineage differentiation potential, cells expressing one or more markers of pluripotent stem cells, hematopoietic, neural, mesenchymal, postpartum, pancreatic, hepatic, retinal epithelial, olfactory bulb, endothelial, muscle, adipose-derived, ileac crest, bone marrow, periodontal ligament, oval and dermal stem cells and organ specific stem cells or progenitor cells, as well as embryonic stem cells.

In some cases the one or more pluripotent stem cell markers include one or more of OCT4, SOX2, UTF1, REX1, OXT2, NANOG, UTF1 AC133, CD9, DNMT3B, FOXD3, ALP, TERT, TERF, FZD9, GCNF, and SCGF.

In some cases the one or more markers are selected from a group consisting of a marker of adipogenic potential, osteogenic potential, neurogenic potential, chondrogenic potential, myogenic potential, and endothelial potential.

Exemplary adipogenic markers include AP0A2, APOD, APOE1 APOC1, and PPARG2. Exemplary osteogenic markers include BMP1, BMP2, OGN, and CTSK. Exemplary neurogenic markers include NTS, NRG1, MBP, MOBP, NCAM1, and CD56. Exemplary chondrogenic markers include COL4, COL5, COL8, CSPG2, and AGC1. Exemplary myogenic markers include MYF5, TMP1, MYH 11. Exemplary endothelial markers include VWF and NOS.

In some cases wherein cells are stem cells said cells may express more than one marker which may be one or more of the following: Oct3/4, Sox2, SSEA-1 (−), SSEA-3 (+), SSEA-4 (+), TRA-1-60 (+), TRA-1-81 (+), lacZ and GFP. The stem cells may be human or non human cells and may possess telomerase activity and a chromosomal methylation pattern characteristic of pluripotential cells.

The cells as used herein may also be immunologically inert cells, such as embryonic or fetal cells, stem cells, and cells genetically engineered to avoid the need for immunosuppression.

In one embodiment, the cells are used immediately upon isolation. In another embodiment, the cells are cryopreserved, allowing their use in a cell bank.

In another embodiment the cells are expanded in culture for a defined period of time, prior to their use for extraction. The time period may be for example, 1-5 population doublings, 5-10 doublings, 10-20 doublings, 20-50 doublings, 50-100 doublings, or more than 100 doublings; alternatively, the period of time in culture may be defined as from 30 minutes to 1 hour, from 1 to 6 hours, from 6-12 hours, from 12-24 hours, from 1-7 days, from 7-30 days, or from 1-6 months and more.

For use in the present invention, cells can be plated directly onto the surface of culture vessels without attachment factors. Alternatively, the vessels can be precoated with natural, recombinant, or synthetic attachment factors or peptides (e.g., collagen or fibronectin, or fragments thereof).

Certain animal cells for culturing according to the present invention may be obtained commercially, for example from ATCC (Rockville, Md.), Cell Systems, Inc. (Kirkland, Wash.), Clonetics Corporation (San Diego, Calif.), BioWhittaker (Walkersville, Md.), or Cascade Biologicals (Portland, Oreg.).

The optimal plating and culture conditions for a given animal cell type can easily be determined by one of ordinary skill in the art using only routine experimentation.

In some cases genetically engineered cells are used, wherein at least one cell of the population of cells is transfected with an exogenous polynucleotide encoding a diagnostic or a therapeutic product which can assist in tissue healing, replacement, maintenance and diagnosis. Some non-limiting examples of such products include—cytokines, growth factors, chemokines, chemotactic peptides, tissue inhibitors of metalloproteinases, hormones, angiogenesis modulators either stimulatory or inhibitory, immune modulatory proteins, neuroprotective and neuroregenerative proteins and apoptosis inhibitors. Some specific exemplary proteins include erythropoietin (EPO), EGF, VEGF, FGF, PDGF, IGF, IFN-α, IFN-β, TGF-α, TGF-β, TNF-α, IL-1, BDNF, GDF-5, BMP-7 and IL-6. The desired gene product can be either constantly or transiently expressed.

In one embodiment, the cells are treated with one or more differentiation agents.

In another embodiment, the cells are treated with one or more epigenetic altering agents.

The cells of the invention can be cultured at all stages of cell cycle. The cells may also be cultured with one or more agents designed to maintain the cell actively in mitosis, for all or part of the time that the cell is maintained in culture. The cells may be exposed to a treatment designed to drive the cell into a particular stage of the cell cycle or to arrest the cell at a particular location in the cell cycle, such as the S, G1, M, or G2 phases, or in a metaphase to anaphase transition cell cycle phase. The cell cycle phase of the cell may be induced by a synchronisation agent. The synchronisation agent may for example be Nocodazole.

Extracts made from cells at a specific phase of the cell life-cycle can contain factors that are preferentially present and active only during that particular phase. Cells collected from a single cell cycle phase can be expected to yield the maximal concentration of the particular factors present only within that phase. For example, during M-phase (mitosis or meiosis) the nuclear envelope is broken down and nuclear and cytoplasm components are found within the same soluble cytosol at physiological concentrations and stoichiometry.

In another embodiment, the cells may be induced to exit the cell cycle and enter G0-Cells in G0 may be obtained directly upon isolation from the animal, or may be obtained from cells that were initially cycling in culture and where then induced to exit the cell cycle by, for example, removal of serum and mitogen factors.

In a specific embodiment, cells may be derived from an animal, expanded in culture as described above, and then induced to enter a particular stage of the cell cycle and stopped, such as G0. The cells may then be maintained in culture prior to the extraction step.

III Cell Culture Conditions

Cells are typically cultivated in a cell incubator at about 37° C. The incubator atmosphere is humidified and contains about 3-10% carbon dioxide in air, although cultivation of certain cell lines may require as much as 20% carbon dioxide in air for optimal results. Culture medium pH is in the range of about 7.1-7.6, about 7.1-7.4, or about 7.1-7.3. Cells in closed or batch culture typically undergo complete medium exchange (i.e., replacing spent media with fresh media) every few days as required by the specific cell type, typically about every 2-3 days. Cells in perfusion culture (e.g., in bioreactors or fermentors) receive fresh media on a continuously recirculating basis.

Culture and differentiation agents useful in this invention include, by way of example, the following: medium refers to culture media for cells, as for example DMEM/F12 (Dulbecco's modified Eaglee's medium/Ham's F12, 1:1, Invitrogen, Carlsbad, Calif.), also encompassing possible alternatives, variations and improvements equivalent to this cell culture medium. In accordance with the particular needs of the cultured cell, the medium may be supplemented with serum preferably at least 5% serum, and more preferably about 15% serum. According to a particular embodiment of the invention, said serum is from bovine origin, more particularly bovine fetal serum, although synthetic and non-synthetic serums, from human and other animals may also be employed, as well as other synthetic or natural reagents, including mixtures thereof, that allow the culture of the cells.

In some cases the medium is serum free medium. In some other cases the cell culture medium may contain antibiotics such as penicillin and streptomycin and/or amino acids such as glutamine and other non-essential amino acids and mixtures thereof. The cells as described herein may be cultured in the presence of a single agent or multiple agents, concurrently or sequentially, for a variable duration of time. The choice of a specific medium depends on the type of cultured cell and is well within the knowledge of a person skilled in the art.

This medium according to the present invention may comprise a) base medium, b) supplements, and c) growth factors. The base medium may include commonly used formulations well known to those skilled in the art including: RPMI, other commonly used basal media and preferably MEM or more preferably the alpha modification of MEM (α-MEM). These base medium also contain commonly used buffers to maintain physiological pH during the cell culture process, including but not limited to, sodium bicarbonate, HEPES and other buffer substances with a pKa in the physiological pH range. Supplements added to the base medium also include those commonly used in cell culture including transferrin or other iron-chelating agents, insulin (including natural or recombinant forms, insulin-like growth factors I & II, and related substances), trace elements, sodium pyruvate, non-essential amino acids, dextran at various molecular sizes, hydrocortisone, ethanolamine, glucose and the tri-peptide, glycyl-histidine-lysine. The appropriate concentrations & compositions for such supplements will be readily apparent to those skilled in the art. Optimal levels of cell culture medium constituents are often determined through an empirical process of testing potential concentrations against a defined endpoint including for example, the growth rate of the cells, etc. The exact formulation of various basal medium supplements may be varied from the list of specific supplements described above while still retaining the specific characteristics of the present invention that primarily includes the ability to support growth of the mesenchymal cell culture. The concentrations and other ingredients in a formulation of standard cell culture medium are well known to those of ordinary skill in the art.

The present invention also contemplates the use of "defined culture media" or "serum-free media" (SFM). A number of SFM formulations are commercially available, such as those designed to support the culture of endothelial cells, keratinocytes, monocytes/macrophages, fibroblasts, chondrocytes, or hepatocytes, which are available from GIBCO/LTI (Gaithersburg, Md.). For example, SFM formulations supporting in vitro culture of keratinocytes have been reported (e.g. U.S. Pat. Nos. 4,673,649 and 4,940,666).

The culture media of the present invention are typically sterilized to prevent unwanted contamination.

The media compositions and formulations of the invention include components which are known to the skilled artisan or can be otherwise deduced using routine methods.

In another embodiment of the invention the cultured cells may be reinforced with exogenously added extracellular matrix proteins, e.g., collagen, laminin, fibronectin, vitronectin, tenascin, integrin, glycosaminoglycan (hyaluronic acid, chondroitin sulfate, dermatan sulfate, heparan sulfate, heparin, keratan sulfate and the like), elastin and fibrin. In some embodiments of the invention growth factors and/or cytokines, such as vascular endothelial cell growth factors, platelet derived growth factors, epidermal growth factors, fibroblast growth factors, hepatocyte growth factors, insulin-like growth factors, and transforming growth factors are exogenously added to the culture.

The cells may be cultured on a surface of glass, ceramic or a surface-treated synthetic polymer. For example, polystyrene that has been subjected to a surface treatment, like γ-ray irradiation or silicon coating, may be used as a surface for cell culture.

Cells which grow to over 85% confluence form cell sheet layer that may be separated from the surface either mechanically, or by using proteolysis enzymes, such as trypsin or dispase. Non-enzymatic cell dissociation could also be used. A non-limiting example includes a mixture of chelators sold under the tradename CELLSTRIPPER (Mediatech, Inc., Herndon, Va.), a non-enzymatic cell dissociation solution designed to gently dislodge adherent cells in culture while reducing the risk of damage associated with enzymatic treatments.

In another embodiment, cells are cultured on a non-adherent surface at sufficient densities. This provides a cell sheet layer that has only a few structural defects as they are recovered with intracellular desmosome structures and the cell-to-cell connectivity and orientation is being kept intact.

In another embodiment, cells are cultured on thermo-responsive dishes supplied for example, by CellSeed, Inc. (Tokyo, Japan).

In this embodiment, the culture surface can be inherently non-adherent or can be rendered non-adherent by surface coatings well known to those skilled in the art. Commercially available cell growth support devices include, for example, the range of Corning® Ultra Low Attachment surface cell culturing products (Corning Inc., Corning N.Y.). These products have a hydrogel layer that is hydrophilic and neutrally charged covalently bound to polystyrene surfaces. Since proteins and other biomolecules passively adsorb to polystyrene surfaces through either hydrophobic or ionic interactions, this hydrogel surface naturally inhibits nonspecific immobilization via these forces, thus inhibiting subsequent cell attachment. Other biocompatible non-adherent materials include ePTFE, polystyrene, stainless steel, and some cross-linked cellulose derivatives. Examples thereof include cross-linked hydroxyalkyl celluloses e.g. hydroxyethyl cellulose, hydroxypropyl cellulose, methyl, thyl and methyl thyl celluloses. Cross-linked carboxyalkyl celluloses also included are carboxymethyl cellulose cross-linked with ethylene glycol diglycidyl ether (EGDGE) or 1,4 butanediol diglycidyl ether. Other materials include polyvinyl alcohol, poly(2-hydroxyethyl methacrylate) (Cellform®) (MP Biomedicals, Irvine, Calif.), agarose, and crosslinked agarose.

Cells can also be seeded into or onto a natural or synthetic three-dimensional support matrix such as a preformed collagen gel or a synthetic biopolymeric material. Use of attachment factors or a support matrix with the medium of the present invention will enhance cultivation of many attachment-dependent cells in the absence of serum supplementation.

The cell seeding densities for each experimental condition can be selected for the specific culture conditions being used. For routine culture in plastic culture vessels, an initial seeding density of, for example, $1\text{-}5\times10^4$ cells per $cm^2$ is useful. In certain cases, micromass cultures are used.

IV—Cell Transfection and Transformation of Cells in Culture

In accordance with the invention cells may be genetically altered by the introduction of a heterologous nucleic acid (e.g. DNA), using various methods known in the art including calcium-phosphate- or DEAE-dextran-mediated transfection, protoplast fusion, electroporation, liposome mediated transfection, direct microinjection and adenoviral or retroviral infection.

In a specific embodiment, a calcium-phosphate precipitate containing DNA encoding the gene(s) of interest can be prepared using the technique of Wigler et al. ((1979) Proc. Natl. Acad. Sci. USA 76:1373-1376). Cultures of adult stem cells (e.g., liver stem cells or adipose stem cells) or their progeny are established in tissue culture dishes. Twenty-four hours after plating the cells, the calcium phosphate precipitate containing approximately 20 μg/ml of the heterologous DNA is added. The cells are incubated at room temperature for 20 minutes. Tissue culture medium containing 3 μM chloroquine is added and the cells are incubated overnight at 37° C. Following transfection, the cells are analyzed for the uptake and expression of the foreign DNA. The cells may be subjected to selection conditions that select for cells that have taken up and expressed a selectable marker gene.

Selectable marker genes include, but are not limited to GFP (green fluorescence protein) or a drug resistance gene. Some non-limiting examples of drug-resistance genes for use in the invention include hygromycin resistance gene, neomycin resistant gene, ampicillin resistance gene, *E. coli* gpt gene or the like.

In another specific embodiment, the heterologous DNA is introduced into a multipotent stem cell using the technique of retroviral transfection. Various processes are known in the art for transferring retroviral vectors into cultured cells. For example, recombinant retroviruses harboring the gene(s) of interest are produced in packaging cell lines to produce culture supernatants having a high titer of virus particles (for example, $10^5\text{-}10^6$ pfu/ml). The recombinant viral particles are used to infect cultures of the stem cells (e.g., adult liver stem cells or adult adipose stem cells) or their progeny by, for example, incubating the cell cultures with medium containing the viral particles and 8 μg/ml polybrene for three hours. Following retroviral infection, the cells are rinsed and cultured in standard medium. The infected cells are then analyzed for the uptake and expression of the heterologous DNA. The cells can be subjected to selective conditions that select for cells that have taken up and expressed a selectable marker gene. Since the gene transferred by the retroviral vector is integrated into chromosomal DNA of the host stem cell, the gene is transmitted to the daughter cell and therefore can be expressed stably over long period.

In certain embodiments the cells described herein, such as adult stem cells (e.g., liver stem cells or mesenchymal stem cells such as adipocyte stem cells), and/or derivatives thereof (e.g., hepatocytes, adipocytes, osteocytes, myoblasts, or chrondrocytes) are immortalized by transformation with an immortalizing gene or construct. Some non-limiting examples of useful immortalizing genes include myc, ras, SV40 T antigen, Ewing's sarcoma oncogene, hTERT, dominant-negative p53, dominant-negative Rb (retinoblastoma), adenovirus EIa, adenovirus EIb, papilloma virus E6, papilloma virus E7, bcr-abl, neu, ret and other immortalizing genes such as Notch.

The cells of the invention can be immortalized by transfection or transduction with a suitable vector, homologous recombination, or other appropriate techniques, so that they express an immortalizing activity (e.g., the telomerase catalytic component (TERT)).

In certain embodiments the immortalizing gene used in accordance with the present invention, or a selection gene, can be inserted between a pair of site-specific recombination sequences so that the gene can be excised when desired. Representative site-specific recombinant sequences include the LoxP sequence, the FRT sequence, or the like. The LoxP sequence is used for performing homologous recombination by the enzyme Cre recombinase.

V—Cell Differentiation and Characterization

Differentiation

In certain embodiments, the present invention encompasses the induction of differentiation of stem cells into specific cell types, such as epithelial cells, stromal cells, cardiac cells, bone cells and more. As is readily apparent to those skilled in the art, there are several methods known and under current development for the differentiation of stem/progenitor cell lines into differentiated target cell types. The present invention is not to be limited by the specific methods used to induce differentiation, but rather includes use of all such methods that are operationally defined as yielding the desired differentiation into a fully differentiated cell type.

For example, U.S. Pat. No. 6,596,274, and U.S. Pat. No. 5,811,094 disclose methods for cell differentiation.

Mesenchymal stem cells can be induced to differentiate into adipocytes, osteocytes, chondrocytes, myocytes, or neuronal cells (e.g., Blanat-Benard et al. (2004) Circ. Res. 94:223). Markers for mesenchymal stem cells and their differentiated cell types are known in the art, for example see Silva et al. (2003) Stem Cells 21:661.

In one specific embodiment, induction of differentiation includes incubating mesenchymal stem cells with a composition comprising IBMX, dexamethasone, indomethasone, and insulin, such that the cell differentiates into an adipocyte. Specifically, Adipocyte induction can be accomplished by culturing mesenchymal stem cells in a medium containing modified MEM with 10% FBS and supplemented with IBMX (I) (500 µM), dexamethasone (D) (1 µM), indomethacin (I) (1 µM), and insulin (I) (10 µg/ml) for three cycles of [IDI-I −2 days, insulin −1 day], and repeating the cycle three times. Successful induction of adipocytes can be determined using, e.g., Oil Red O staining of lipid vacuoles.

In yet another embodiment, the differentiation composition includes dexamethasone, L-ascorbate-2-phosphate, and β-glycerophosphate, such that the cell differentiates into an osteocyte. Specifically, induction of osteocyte differentiation is achieved by culturing stem cells in a medium composed of modified MEM with 10% FBS and supplemented with dexamethasone (0.1 µM), L-ascorbate-2-phosphate (50 µM), and β-glycerophosphate (10 mM) for about four weeks. Osteocytes can be identified by the presence of calcified extracellular matrix (ECM) using Von Kossa staining.

In yet another embodiment, the differentiation composition includes TGF-β1, L-ascorbate-2-phosphate, and insulin, such that the cell differentiates into a chondrocyte. Specifically, chondrogenic differentiation can be achieved by culturing mesenchymal stem cells in micromass culture using a medium composed of modified MEM containing 10% FBS and supplemented with TGF-β1 (10 ng/ml), L-ascorbate-2-phosphate (50 µM), and insulin (6.25 µg/ml). Cells with characteristics of chondrocytes generally develop in about one week and can be identified, e.g., using Alcian blue (pH 1.0) staining, which detects the presence of proteoglycans.

Myogenic differentiation can be induced, e.g., by culturing mesenchymal stem cells in modified MEM containing 5% horse serum and supplemented with 50 µM hydrocortisone for four to six weeks. Differentiated cells can be identified, e.g., by immunostaining with an antibody that specifically recognizes skeletal myosin.

The methods of inducing differentiation that are described herein are exemplary and are not intended to be limiting. Other suitable methods of identifying specific differentiated cell types are known in the art and can be used to identify differentiated cells obtained from adult stem cells cultured using the methods described herein.

Characterization

The process of making a differentiated cell from a stem cell is accompanied by changes in the expression of cell markers. There are also unique pluripotent stem cells markers as well as markers of multilineage differentiation. Such cell markers are typically expressed as mRNA and/or protein. Detection of the mRNA or protein markers may be performed by any method known in the art. In some embodiments, nucleic acids and/or proteins will be isolated from the cells and then analyzed.

Tissue-specific protein markers can be detected using any suitable immunological technique such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium.

The expression of tissue-specific markers can also be detected at the mRNA level by Northern blot analysis, dot-blot hybridization analysis, or by reverse transcriptase initiated polymerase chain reaction (RT-PCR) using sequence-specific primers in standard amplification methods. See for example, U.S. Pat. No. 5,843,780. Sequence data for the particular markers can be obtained from public databases such as GenBank (URL www.ncbi.nlm.nih.gov:80/entrez). Expression of tissue-specific markers as detected at the protein or mRNA level is considered positive if the level is at least 2-fold, and, in certain instances, more than 10- or 50-fold above that of a control cell, such as an undifferentiated adult liver stem cell, a fibroblast, or other unrelated cell type.

VI. Engineered Tissues

The present invention also contemplates use of engineered tissues as a source for preparing tissue extract for constructing biologically active scaffolds. A variety of tissue engineering techniques are known, including tissue in-growth, seeding of cells on artificial or biodegradable scaffolds and collagen gels, and tissue "self-assembly". In the self-assembly method, cells are induced to secrete and organize an extracellular matrix and thereby form a sheet of living tissue. The self-assembly method takes advantage of the fact that cells such as fibroblasts can produce a suitable extracellular matrix when grown in the presence of ascorbic acid. To create multi-layer tissue constructs, sheets of living tissue can be stacked upon each other, folded upon themselves, or rolled on a tubular support.

The engineered tissue in accordance with the present invention is formed from at least one sheet of living tissue. Each sheet of living tissue is comprised of cells and an endogenous extracellular matrix. The extracellular matrix is secreted by cells, such as mesenchymal cells, embryonic stem cells or adult stem cells.

In a certain embodiment, when mesenchymal cells, such as dermal fibroblasts, are cultured in a planar culture substratum using L-ascorbic acid or a phosphate derivative of L-ascorbic acid (e.g. Asc 2-P), serum, and growth factors, they show an abundant synthesis of extracellular matrix proteins. This creates the basis of the endogenous extracellular matrix. L-ascorbic acid plays an important role since it is a cofactor for the hydroxylation of proline and lysine residues in collagen, and also it increases both the rate of transcription of procollagen genes and stability of procollagen mRNA. The extracellular material is comprised of different proteins, such as collagen type I, other collagen types (fibrillar and non-fibrillar), elastin, fibrillin, glycosaminoglycans (such as decorin), growth factors, and glycoproteins.

An exemplary embodiment of methodology for generating such sheets of living tissue is described in U.S. Pat. No. 5,618,718 by Auger et al. In summary, Auger et al. describe that smooth muscle cells, at a concentration equivalent to $10^4$ cells/cm$^2$, are plated into 75 cm$^2$ sterile Petri dishes. Cell medium is supplemented with a 3:1 DMEM and Ham's F12 modified medium, fetal bovine serum, penicillin and gentamicin, and with an ascorbic acid solution. For example, a final ascorbic acid solution between 50-100 μg/ml can be used every other day. Culture conditions are kept at 92% air and 8% CO2 at full humidity. Culture time is approximately three weeks. At the end of the maturation time, the sheet of living tissue spontaneously detaches from the substratum.

It can be appreciated that a variety of methods can be used to prepare the sheets of living tissue and the present invention is not limited in scope by using one particular shape (i.e. thickness and size), cell type, origin, age, maturation time, component concentration, and culture conditions to generate the sheet of living tissue.

To produce a sheet layer, a cell population (homogenous or heterogeneous) is cultured on a non-adherent substrate in the presence of commonly available culture media components, to promote extracellular matrix protein production. After an extended culture period, enough extracellular matrix protein is produced to make a coherent cell sheet.

Cells can be seeded at different densities sufficient to permit the formation of cell sheet layer. This will vary for different cell types and will need to be optimized. In the case of chondrocytes, the cell densities can range from 1,000 cells/cm$^2$ to 100,000 cells/cm$^2$.

Appropriate culture medium (for example, DMEM medium, MEM medium, HamF12 medium, HamF10 medium) is added. Cells of the required density are then added so that cells settle to the bottom of the dish. Alternatively cells of the required number can be suspended in the culture medium and added. In this case, cells will not attach to the bottom of the dish, and cell-to-cell adhesion creates cell sheet layer. Cultures are maintained for a few days to a few weeks before cell sheet layer can be recovered. During culture, the culture medium may be exchanged, if needed. Usually, the culture medium is exchanged every 0.6 to 2 days of the culture. The addition of agents that promote cell growth, viability and/or cell-to-cell adhesion can be used during the culture process. For example, addition of agents such as ascorbic acid, retinoic acid, and copper can be used to increase the production of extracellular matrix proteins thereby generating a more robust sheet layer. Growth factors capable of stimulation of extracellular matrix protein production could be used or a combination of growth factors, microelements, vitamins and such.

Cell sheet layer can be recovered by gently peeling cell sheet layer using a pair of forceps. Alternatively, cell sheet layer is brought into close contact with a polymer membrane such that cell sheet layer adheres to the polymer sheet. The coupled cell sheet/polymer backing can then be removed with a pair of tweezers. Peeling of cell sheet layer can be performed not only in the culture solution used to culture cells, but also in other isotonic solutions. A suitable solution can be chosen in accordance with a specific object. Examples of the polymer membrane that can be used to achieve close contact with cell sheet layer include polyvinylidene difluoride (PVDF), polypropylene, polyethylene, cellulose and its derivatives, as well as chitin, chitosan, collagen, polyurethane, and other such films or meshes made with known bioresorbable natural and synthetic polymers. The backing layer may be continuous or apertured (formed into a net). The backing layer may be flat or contoured. The contours may be produced for example by embossing. Suitably contoured films may also have apertures.

The tissue sheet may comprise any number of various cell types. Cells including, for example, fibroblasts may be derived from a number of organs including, for example, the skin, pancreas, liver, and the like.

Robust tissue sheets are special constructs. They are different from other standard cell cultures in many ways both structurally and physically. Structurally: 1) tissue sheets are composed of multiple layers of cells, 2) the cells are embedded in a large amount of extracellular matrix proteins produced by the cells themselves, 3) the extracellular matrix proteins are "natural" in as much as they are not physically/chemically modified by extraction/isolation, procedures, 4) the extracellular matrix proteins are of various types and offer a complex extracellular environment to the cells (similar to a physiological tissue environment), 5) the tridimensional organization of the extracellular protein matrix is also similar to the physiological tissue environment. Physically: 1) the tissue sheets are thick (~50 to 200 μm) compared to a monolayer (~5 μm thick) and are easily visible to the naked eye; 2) they can be peeled off a culture substrate with regular tweezers, 3) they are peeled off the culture substrate as one single, intact sheet covering the entire culture surface and containing practically all the cells of the culture and the extracellular matrix proteins produced by the cells, 4) these sheets are robust enough that they can be easily manipulated with common surgical instruments, 5) these robust tissue sheets have show a resistance to puncture (WO 03/050266).

The engineered tissue of the invention may be used as such for the extraction process, or alternatively, cells may be substantially eliminated from the scaffold prior to the extraction step. Cells may be eliminated from the engineered tissue using any of the methods described in Section IX below.

VII. Extract Preparation

Extract preparation may be done by any suitable method known in the art.

According to certain embodiments, a first step in extract preparation is cell disruption, which may be performed using one of the following non-limiting options: enzyme digestion, homogenization, sonication, Bead mill, mincing, mechanical grinding with abrasive materials, French press, or detergents.

Extraction is typically performed in the presence of an extraction buffer (also referred to as extraction medium). The extraction buffer is designed for maintaining the structure and function of the extract components. This may be achieved by including ribonuclease inhibitors and/or protease inhibitors and reducing agents (e.g. antioxidants) in the buffer, by maintaining a defined pH, cation strength, and salt concentration, and by keeping the buffer at a cold temperature.

The inclusion of ribonuclease inhibitors and/or protease inhibitors in the buffer or the extract is aimed at preventing or minimizing degradation of RNAs and/or proteins by cellular ribonucleases and/or proteases.

The inclusion of antioxidants in the buffer or the extract is aimed, for example dithiothreitol (preferably at 0.5-5 mM) and/or 3-mercaptoethanol (preferably at 100-500 mM), is aimed at preventing or minimizing inactivation of factors through oxidation.

The buffer or the extract may also be supplemented with an agent which inhibits protein dephosphorylation, for example, glycerophosphate and/or vanadate. Addition of such an agent is aimed at preventing or minimizing inactivation of factors through protein dephosphorylation.

The buffer or the extract may be supplemented with an energy regeneration system/mix comprising creatine kinase (for example at 50-100 µg/ml) and/or creatine phosphate (for example at 10-20 mM) and/or ATP (for example at 1-2 mM) and/or GTP (for example at 1-2 mM) and/or $MgCl_2$ (for example at 1 mM). The energy regeneration mix supplements biochemical energy in vitro.

The buffer or the extract may be supplemented with an agent that stabilizes the extract and/or buffer, for example glycerol and/or sucrose (preferably at 5-50% v/v). Stabilizing the buffer or the extract refers both to the preparation stage and the storage period.

The extracts used in the present invention can be prepared from whole cells or tissues (including cells and extracellular matrix components), or from specific cellular compartments e.g. a cytoplasmic compartment or a nuclear compartment, and comprise amino acids, peptides, polypeptides, proteins, carbohydrates, lipids, nucleic acids, glycoproteins, lipoproteins, glycolipids, glycosaminoglycans, and proteoglycans. Proteins include for example, chromatin remodelling complexes, such as BRG1 or Brahma, HDACs, histone methyl transferases, histones acetyl transferases, hydroxylases, signalling molecules, and transcription factors, such as SP1. Lipid components may include phosphoinositides, such as PIP2, IP3, and IP4. Nucleic acids/nucleotides may include RNA, DNA, cAMP, cGMP.

Extracellular matrix components include but are not limited to collagen, fibrin, fibrinogen, thrombin, elastin, laminin, fibronectin, hyaluronic acid, chondroitin 4-sulfate, chondroitin 6-sulfate, dermatan sulfate, heparin sulfate, heparin, and keratan sulfate, and proteoglycans.

In some embodiments the extract is compartmentalized prior to further use. For example, nuclear extract, cytoplasmic extract, or whole cell extracts may be used, as well as any combinations thereof. Any of these may be fractionated on density gradients.

A particular embodiment of the present invention is an extract comprising the intracellular compartment of pluripotent stem cells. The pluripotent stem cells are preferably undifferentiated. Furthermore, the pluripotent stem cells are preferably of mammalian origin, more preferably of human origin.

The intracellular compartmental extract is prepared according to methods well-known in the art; see e.g. WO/2002/097065. The extract may comprise other constituents which improve its function.

Nuclear factors may be obtained from a karyoplast isolated from the cell. Alternatively, the nuclear factors may be obtained from a nucleus isolated from the karyoplast or the cell.

The nuclear membrane of the cell, of the karyoplast or of the isolated nucleus may be disrupted to release nuclear factors. The nuclear membrane may be disrupted by sonication, by isotonic bursting, and/or by using a homogenizer, or by other methods known in the art.

The extract may be prepared from a cell which has been pre-treated with an agent that causes enucleation. For example the agent may be cytochalasin, preferably cytochalasin B or D. Such agents inhibit intermediate filament production and stabilization, thereby aiding release of the mitotic/meiotic spindle or nucleus from the cell.

The extract may be provided as enucleated whole cytoplasm. Alternatively, the extract may be provided as a derivative of the cytoplasm of the cell. In a further embodiment, the extract is provided as a derivative of an isolated karyoplast.

The extract and/or medium may be supplemented with an agent that stabilizes the extract and/or medium, for example glycerol and/or sucrose (preferably at 5-50% v/v). Stabilization may be during preparation of the extract and/or medium or during storage.

VIII. Scaffold Fabrication

The present invention provides methods of making a biologically active scaffold composed of cell extracts (obtained for example by the methods described above). The isolated extracts are being used as the starting material/substrate for the scaffold fabrication process.

In one embodiment, the biologically active scaffold is capable of supporting cell growth. In another embodiment, the biologically active scaffold is capable of supporting cell differentiation. In another embodiment, the biologically active scaffold is capable of supporting the maintenance of a differentiation state of a cell. In one embodiment, the biologically active scaffold further comprises a cell. In another embodiment, the cell is genetically modified. The biologically active scaffold can be used as tissue engineering scaffold and implanted into the body to replace/repair damaged/non-functional tissues.

The fabrication process of the biologically active scaffold can be done by any technique know in the art, such as solvent-casting and particulate-leaching, gas foaming, fiber meshes/fiber bonding, filament drawing, phase separation, melt molding, compression molding, emulsion freeze drying, solution casting, coating, weaving, electrospinning and freeze drying, thereby producing scaffolds with various pore size, interconnectivity and architecture.

In a preferred embodiment, the invention provides a method of making a biologically active scaffold composed of a cell extract, wherein the extract is electroprocessed to produce electroprocessed fibers. The method comprises obtaining an extract and dissolving the extract in a solvent to produce a solution; and subjecting the solution to electroprocessing to produced electroprocessed fibers.

In one embodiment, the step of electroprocessing is performed by electrospinning; and the electroprocessed fibers are electrospun fibers.

In certain embodiments, the electrospinning process of the present invention uses a simple electrospinning technique and therefore is easy to use and is cost effective.

Electrospinning is an atomization process of a conducting fluid which exploits the interactions between an electrostatic field and the conducting fluid. When an external electrostatic field is applied to a conducting fluid (e.g., a semi-dilute polymer solution or a polymer melt), a suspended conical droplet is formed, whereby the surface tension of the droplet is in equilibrium with the electric field. Electrostatic atomization occurs when the electrostatic field is strong enough to overcome the surface tension of the liquid. The liquid droplet then becomes unstable and a tiny jet is ejected from the surface of the droplet. As it reaches a grounded target, the material can be collected as an interconnected web containing relatively fine, i.e. small diameter, fibers. The resulting films (or membranes) from these small diameter fibers have very large surface area to volume ratios and small pore sizes. A detailed description of electrospinning apparatus is provided in Zong, X., 2005 Biomaterials 26: 5330-8. After electrospinninng, extrusion and molding can be utilized to further fashion the polymers. To modulate fiber organization into aligned fibrous polymer scaffolds, the use of patterned electrodes, wire drum collectors, or post-processing methods such as uniaxial stretching has been successful (Zong, X., supra).

The extract used to form an electro-spun scaffold is first dissolved in a solvent. In one embodiment, the solvent is selected from the group consisting of an organic solvent, an acid, a base, an alcohol, and any combination thereof. Typical solvents include N,N-Dimethyl formamide (DMF), tetrahydrofuran (THF), methylene chloride, dioxane, ethanol, hexafluoroisopropanol (HFIP), chloroform, 1,1,1,3,3,3-hexafluoro-2-propanol (HFP), glacial acetic acid, water, and combinations thereof.

The extract solution may optionally contain a salt which creates an excess charge effect to facilitate the electrospinning process. Examples of suitable salts include NaCl, $KH_2PO_4$, $K_2HPO_4$, $KIO_3$, KCl, $MgSO_4$, $MgCl_2$, $NaHCO_3$, $CaCl_2$ or mixtures of these salts. The extract solution forming the conducting fluid preferably has a protein concentration in the range of about 1 to about 80% wt, more preferably about 8 to about 60% wt.

The electric field created in the electrospinning process preferably is in the range of about 5 to about 100 kilovolts (kV), more preferably about 10 to about 50 kV.

The feed rate of the conducting fluid to the spinneret (or electrode) preferably is in the range of about 0.1 to about 1000 μl/min, more preferably about 1 to about 250 μl/min.

The single or multiple spinnerets are located on a platform which is capable of being adjusted, varying the distance between the platform and the grounded collector substrate. The distance can be any distance which allows the solvent to essentially completely evaporate prior to the contact of the polymer with the grounded collector substrate. In an exemplary embodiment, this distance can vary from 1 cm to 25 cm. Increasing the distance between the grounded collector substrate and the platform generally produces thinner fibers.

In electrospinning cases where a rotating mandrel is required, the mandrel is mechanically attached to a motor, often through a drill chuck. In an exemplary embodiment, the motor rotates the mandrel at a speed of between about 1 revolution per minute (rpm) to about 500 rpm. In an exemplary embodiment, the motor rotation speed of between about 200 rpm to about 500 rpm. In another exemplary embodiment, the motor rotation speed of between about 1 rpm to about 100 rpm.

It is to be understood that the electroprocessed extracts may be combined with other natural and/or synthetic materials and/or substances in forming the scaffolds of the present invention.

Various characteristics of the scaffold can be manipulated by adding various components to the cell extract-based scaffold. For example, incorporation of durable synthetic polymers (e.g. PLA, PGA) may increase the durability and structural strength of scaffolds electroprocessed from solutions of cells or tissue extracts.

Accordingly, selection of materials for electroprocessing and use in substance delivery is influenced by the desired use.

In addition, a combination of one or more of therapeutic agents, analgesics, anesthetics and anti-rejection substances may be incorporated into the scaffold.

In one embodiment, substances can be released from the scaffold in a controlled delayed-release fashion.

For example, layered or laminate structures can be used to control the substance release profile. Unlayered structures can also be used, in which case the release is controlled by the relative stability of each component of the construct. For example, layered structures composed of alternating electroprocessed materials are prepared by sequentially electroprocessing different materials onto a target. The outer layers are, for example, tailored to dissolve faster or slower than the inner layers. Multiple agents can be delivered by this method, optionally at different release rates. Layers can be tailored to provide a complex, multi-kinetic release profile of a single agent over time. Using combinations of the foregoing provides for release of multiple substances released, each with its own profile. Complex profiles are possible.

Natural components such as biocompatible substances can be used to modulate the release of electroprocessed materials or of substances from an electroprocessed scaffold. For example, a drug or series of drugs or other materials or substances to be released in a controlled fashion can be electroprocessed into a series of layers. In one embodiment, one layer is composed of electroprocessed extract-derived components plus a drug, the next layer PLA plus a drug, a third layer is composed of polycaprolactone plus a drug. The layered construct can be implanted, and as the successive layers dissolve or break down, the drug (or drugs) is released in turn as each successive layer erodes. In some embodiments, unlayered structures are used, and release is controlled by the relative stability of each component of the scaffold.

In solvent casting, a solution of one or more proteins in an appropriate solvent, is cast as a branching pattern relief structure. After solvent evaporation, a thin film is obtained.

In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the artificial organ. Next a solvent is used to dissolve away one of the components, resulting in pore formation. (See U.S. Pat. No. 5,514,378).

The biological scaffold may be shaped into any number of desirable configurations to satisfy any number of overall system, geometry or space restrictions. For example, in the use of the biological scaffold for bladder, urethra, valve, or blood vessel reconstruction, the matrix or scaffold may be shaped to conform to the dimensions and shapes of the whole or a part of the tissue. The biological scaffold may be shaped in different sizes and shapes to conform to the organs of differently sized patients. For bladders, the scaffold should be shaped such that after its biodegradation, the resulting reconstructed bladder may be collapsible when empty in a fashion similar to a natural bladder. The biological scaffold may also be shaped in other fashions to accommodate the special needs of the patient.

IX. Cell Seeding and Redesigning the Biological Scaffolds

In one embodiment of the invention, the biological scaffolds are seeded with one or more types of cell populations to allow said cells to interact in a molecular, structural and functional way with the scaffold, e.g. to form an ECM upon the scaffold and to secret various soluble factors, thereby supplementing the scaffold with additional agents. The cells can be derived from various sources, for example mammals such as humans, monkeys, dogs, cats, mice, rats, cows, horses, pigs, goats and sheep.

In a preferred embodiment, about 5,000 cells to 500 million cells are suspended in medium and applied to each square centimeter of a surface of a scaffold. Preferably, between 50,000 and 50 million cells, and more preferably, between 50,000 and 5 million cells are suspended in media and applied to each square centimeter of a surface of a scaffold. The scaffold is incubated under standard culturing conditions, such as, for example, 37° C., 5% CO2, for a period of time until the cells attach. It will be appreciated that the density of cells seeded onto the scaffold can be varied. Other seeding techniques may also be used depending on the scaffold and the cells. For example, the cells may be applied to the scaffold by vacuum filtration. Selection of cell types, and seeding of cells onto a scaffold, will be routine to one of ordinary skill in the art in light of the teachings herein.

In one embodiment, the scaffolds are seeded with one population of cells. In another embodiment, the scaffold is seeded on two sides with two different populations of cells. This may be performed by first seeding one side of the scaffold and then seeding on the other side. For example, the scaffold may be placed with one side on top and seeded. Then the scaffold may be repositioned so that a second side is on top. The second side may then be seeded with a second population of cells. Alternatively, both sides of the scaffold may be seeded at the same time. For example, two cell chambers may be positioned on both sides (i.e., a sandwich) of the scaffold. The two chambers may be filled with different cell populations to seed both sides of the matrix or scaffold simultaneously. The sandwiched scaffold may be rotated, or flipped frequently to allow equal attachment opportunity for both cell populations. Simultaneous seeding may be preferred when the pores of the scaffold are sufficiently large for cell passage from one side to the other side. Seeding the scaffold on both sides simultaneously can reduce the likelihood that the cells would migrate to the opposite side.

In another embodiment, two separate scaffolds are seeded with different cell populations. After seeding, the two scaffolds may be attached together to form a single scaffold with two different cell populations on the two sides. Attachment of the scaffolds to each other may be performed using standard procedures such as fibrin glue, liquid co-polymers, sutures and the like.

In order to facilitate cell growth on the scaffold of the present invention, the scaffold may be coated with one or more cell adhesion-enhancing agents. These agents include but are not limited collagen, laminin, and fibronectin.

In addition, the cells may be cultured onto the scaffold in the presence of agents that promote cellular proliferation and growth. Such agents include a number of growth factors that can be selected based upon the cell types present (non limiting examples include: keratinocyte growth factor (KGF); vascular endothelial cell growth factor (VEGF); platelet derived growth factor (PDGF); fibroblast growth factor (FGF); transforming growth factor (TGF) α, β, and the like; insulin; growth hormone; colony stimulating factors; erythropoietin; epidermal growth factor (EGF); and hepatic erythropoietic factor (hepatopoietin)). Serum, such as fetal bovine serum (FBS) or the like, can also provide some of these growth factors. In addition, agents such as ascorbic acid can be used to increase extracellular matrix production.

In another aspect, cells are substantially eliminated from the seeded biological scaffolds of the invention prior to further use to provide a cell-free scaffold enriched and conditioned with extracellular matrix components and secreted factors provided by the population of seeded cells. A cell-free scaffold may have a reduced level of immunogenicity, and may provide an appropriate matrix for host cell repopulation or secondary cell seeding.

Cells may be eliminated from the seeded scaffold, for example by air-drying or lypholization to kill the cells. Thermal shock, radiation, acoustic treatment, changes in pH, mechanical disruption, addition of toxins, detergents (SDS or triton x100), enzymes (RNAase, DNAase, protease, lipase), or solvents (alcohol, acetone, or chloroform) may also be used. In addition, treatment with hypotonic or hypertonic solutions, which have nonphysiological ionic strengths, can also promote the cell elimination process. See, for example, WO 9603093 and WO 9632905.

In another embodiment, the biological scaffolds can go through one or more rounds of redesigning (by seeding the same or different types of cells) followed by cell elimination.

As used herein the term "redesigning" refers to the modification of the scaffold by the seeded cells. This modification occurs at the structural and functional level and is a result of a dynamic interaction between the seeded cells and the scaffold. Redesigning includes for example global reshaping of the architecture and integration of newly synthesized matrix elements. Redesigning may improve the physical and biological characteristics of the scaffold, as well as the matching of the scaffold to treat a specific target tissue or a specific patient, by seeding tissue-specific cells or by seeding cells which are autologous to a patient.

Redesigning can also be done by serially seeding several types of cells, or simultaneously by seeding a mixed population of several types of cells, followed by the elimination of the cells by any suitable technique.

X. 3D Architecture Design, Reinforcement with External Scaffolds

The scaffold of the invention can be provided as an injectable scaffold or as a transplantable scaffold.

The Injectable Form:

The scaffold of the present invention can also be formed into an injectable gel, suspension or solution by any suitable method known in the art, for example in a manner similar to that described in WO 08/109,407.

Additionally, the scaffold can be first formed into a powder by tearing, cutting, grinding, optionally frozen, in a manner similar to that described in WO 98/25636. The powder can be further solubilized or suspended with a gel compound or a physiological solution and formulated into a hydrophilic injectable gel.

For example, in orthopedic applications, the injectable form of the scaffold of the invention can be used to repair bone tissue, for instance using the general techniques described in U.S. Pat. No. 5,641,518. Thus, a powder form of the scaffold can be implanted into a damaged or diseased bone region for repair. The powder can be used alone, or in combination with one or more additional bioactive agents such as physiologically compatible minerals, growth factors, antibiotics, chemotherapeutic agents, antigen, antibodies, enzymes, vectors for gene delivery and hormones.

The injectable scaffold of the invention may be administered to an individual in need thereof in a wide variety of ways. Preferred modes of administration include intravenous, intravascular, intramuscular, subcutaneous, intracerebral, intraperitoneal, soft tissue injection, surgical placement, arthroscopic placement, and percutaneous insertion, e.g. direct injection, cannulation or catheterization. Most preferred methods result in localized administration of the inventive composition to the site or sites of tissue defect. Any administration may be a single application of a composition of invention or multiple applications. Administrations may be to single site or to more than one site in the individual to be treated. Multiple administrations may occur essentially at the same time or separated in time.

Figure 3A:
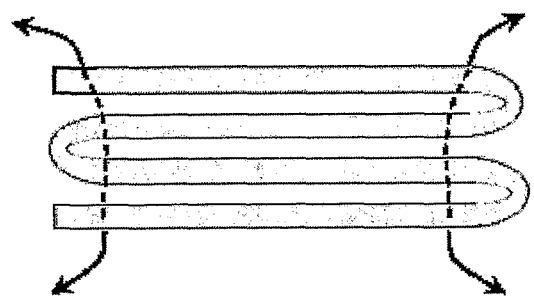
FIG. 3 is a schematic representation of various 3D structures obtainable with the scaffold of the invention.
Figure 3B:
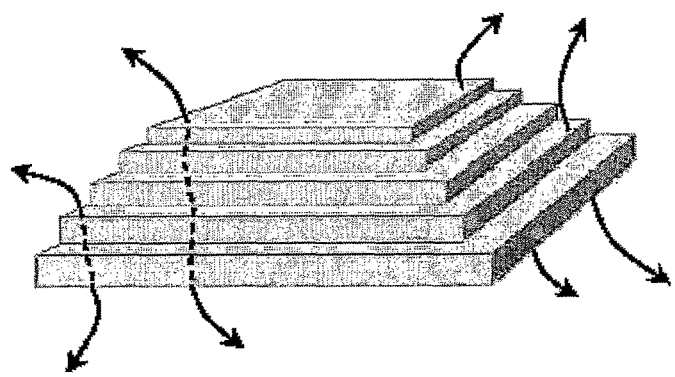
Figure 3C:
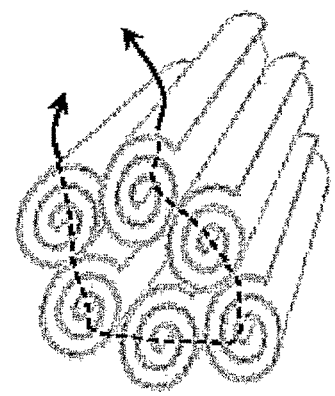
Figure 3D:
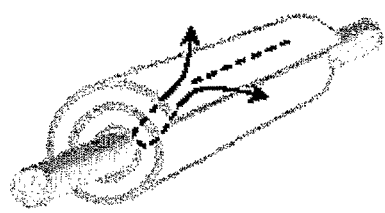

The transplantable form of the scaffold of the invention can be provided as a sheet, which can be trimmed to a desirable size. The sheet or the combination of several sheets can be configured to form any 3D shape as described in FIG. 3. FIG. 3A shows a scaffold which is folded upon itself one or more times. FIG. 3B shows scaffolds that are arranged in layers. FIG. 3C shows a scaffold which is rolled upon itself one or more times. Several rolled scaffolds are placed next to each other. FIG. 3D shows a scaffold which is folded upon an object (such as a tubular object) one or more times. In all cases arrows indicate sutures which may be placed in order to maintain the integrity of the construct.

Larger area sheets can be prepared by fusing together several smaller area sheets. Sheets can be fused together by compressing their overlapped edges under dehydrating conditions. In addition, the sheets can be joined by standard tissue bonding techniques known to those skilled in the art, including the use of sutures, crosslinking agents, adhesives and pastes.

One of ordinary skill in the art will appreciate that one or more layers of the biological scaffold may be used in accordance with the invention. In addition, scaffold layers of the same structure and chemistry or different structures and chemistries can be overlaid on top of one another to achieve superior mechanical strength. The scaffold might provide additional benefit since it might incorporate a genetic material, cytokines, and growth factors to promote survival, proliferation, and differentiation of cells. Various means of incorporation of these beneficial factors into the scaffold are known to those skilled in the art including but not limited to coating.

When layering several scaffolds, the scaffolds are held together by surface adhesion between the sheets. Any number of scaffolds may be used, preferably five or more, more preferably seven or more, and more preferably, nine, ten, eleven or more. The scaffolds are delicately handled with forceps and superimposed or otherwise assembled to form the construct. By maintaining this construct in culture medium supplemented with ascorbic acid, the scaffolds will fuse together to form an engineered tissue resembling the corresponding mature tissue.

Other methods of holding scaffolds together include, without limitation: suturing, sewing, gluing, hooking, clamping, riveting etc.

The scaffold is a three-dimensional structure or framework. The scaffold may be configured into various shapes such as generally flat, generally cylindrical or tubular, or can be completely free-form as may be required or desired for the corrective structure under consideration.

The scaffold may optionally be cross-linked using any cross-linking agent known in the art. Such cross-linking can increase longevity and inhibit enzymatic degradation of the scaffold by the host.

The biological scaffolds of the invention can further comprise biodegradable or non-biodegradable reinforcing elements, also termed herein scaffold-enhancing agents.

The scaffold-enhancing agents may be added at the scaffold preparation step, e.g. during electro-spinning, or applied onto the scaffold after it is formulated.

Reinforcing elements include, but are not limited to, textile structures such as weaves, knits, braids, perforated films, meshes, and non-wovens. An example of a reinforcing element is a knitted or non-woven mesh comprised of poly(glycolic acid-co-lactic acid) copolymer, or PGA/PLA, fibers sold under the tradename VICRYL (Ethicon, Inc., Somerville, N.J.).

In embodiments where the scaffold further comprises at least one synthetic polymer, suitable biocompatible synthetic polymers can include polymers selected from the group consisting of aliphatic polyesters, copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polypropylene fumarate), polyurethane, poly(ester urethane), poly(ether urethane), and blends and copolymers thereof. Suitable synthetic polymers for use as additives to the scaffold in accordance with the present invention can also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides and combinations thereof.

For the purpose of this invention aliphatic polyesters include, but are not limited to, homopolymers and copolymers of monomers including lactide (which includes lactic acid, D-, L- and meso lactide); glycolide (including glycolic acid); epsilon-caprolactone; p-dioxanone(1,4-dioxan-2-one); trimethylene carbonate(1,3-dioxan-2-one); alkyl derivatives of trimethylene carbonate; and blends thereof. Aliphatic polyesters can be homopolymers or copolymers (random, block, segmented, tapered blocks, graft, triblock, etc.) having a linear, branched, or star structure.

In embodiments where the scaffold includes as an additive at least one natural polymer, suitable examples of natural polymers include, but are not limited to, fibrin-based materials, collagen-based materials, hyaluronic acid-based materials, glycoprotein-based materials, cellulose-based materials, silks and combinations thereof. By way of non-limiting example, the biocompatible scaffold can include a collagen-based small intestine submucosa, periosteal membrane, synovial or amniotic membrane.

One skilled in the art will appreciate that the selection of a suitable material for adding to the scaffold of the present invention depends on several factors. These factors include in vivo mechanical performance; cell response to the material in terms of cell attachment, proliferation, migration, and differentiation; biocompatibility; and optionally, biodegradation kinetics. Other relevant factors include the chemical composition, spatial distribution of the constituents, the molecular weight of the polymer, and the degree of crystallinity.

The scaffolds may also be prepared or incorporated with agents that protect against shrinkage of the scaffold, as well as with agents which provide flexibility, e.g. collagen cross-linking inhibitors.

XI. Diseases, Disorders or Conditions

Examples of diseases, disorders, or conditions that may be treated using the scaffolds of the invention include neurological, endocrine, structural, skeletal, vascular, urinary, digestive, integumentary, blood, immune, auto-immune, inflammatory, endocrine, kidney, bladder, cardiovascular, cancer, circulatory, digestive, hematopoeitic, and muscular diseases, disorders, and conditions. In addition, pluripotent stem cells or reprogrammed cells may be used for reconstructive applications, such as for repairing or replacing tissues or organs. Examples of medical applications for pluripotent stem cells or reprogrammed cells include the administration of neuronal cells to an appropriate area in the human nervous system to treat, prevent, or stabilize a neurological disease such as Alzheimer's disease, Parkinson's disease, Huntington's disease, or ALS; or a spinal cord injury. In particular; degenerating or injured neuronal cells may be replaced by the corresponding cells from a mammal, derived directly or indirectly from pluripotent stem cells or reprogrammed cells. This transplantation method may also be used to treat, prevent, or stabilize autoimmune diseases including, but not limited to, insulin dependent diabetes mellitus, rheumatoid arthritis, pemphigus vulgaris, multiple sclerosis, and myasthenia gravis. In these procedures, the cells that are attacked by the recipient's own immune system may be replaced by transplanted cells. In particular, insulin-producing cells may be administered to the mammal for the treatment or prevention of diabetes, or oligodendroglial precursor cells may be transplanted for the treatment or prevention of multiple sclerosis. For the treatment or prevention of endocrine conditions, reprogrammed cells that produce a hormone, such as a growth factor, thyroid hormone, thyroid-stimulating hormone, parathyroid hormone, steroid, serotonin, epinephrine, or norepinephrine may be administered to a mammal. Additionally, reprogrammed epithelial cells may be administered to repair damage to the lining of a body cavity or organ, such as a lung, gut, exocrine gland, or urogenital tract. It is also contemplated that reprogrammed cells may be administered to a mammal to treat damage or deficiency of cells in an organ such as the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, or uterus.

Pluripotent and reprogrammed cells may also be combined with a matrix to form a tissue or organ in vitro or in vivo that may be used to repair or replace a tissue or organ in a recipient mammal. For example, pluripotent and reprogrammed cells may be cultured in vitro in the presence of a matrix to produce a tissue or organ of the urogenital system, such as the bladder, clitoris, corpus cavermosum, kidney, testis, ureter, uretal valve, or urethra, which may then be transplanted into a mammal (Atala, Curr. Opin. Urol. 9(6): 517-526, 1999). In another transplant application, synthetic blood vessels are formed in vitro by culturing pluripotent and reprogrammed cells in the presence of an appropriate matrix, and then the vessels are transplanted into a mammal for the treatment or prevention of a cardiovascular or circulatory condition. For the generation of donor cartilage or bone tissue, pluripotent and reprogrammed cells such as chondrocytes or osteocytes are cultured in vitro in the presence of a matrix under conditions that allow the formation of cartilage or bone, and then the matrix containing the donor tissue is administered to a mammal. Alternatively, a mixture of the cells and a matrix may be administered to a mammal for the formation of the desired tissue in vivo. The cells may be attached to the surface of the matrix or encapsulated by the matrix. Examples of matrices that may be used for the formation of donor tissues or organs include collagen matrices, carbon fibers, polyvinyl alcohol sponges, acrylateamide sponges, fibrin-thrombin gels, hyaluronic acid-based polymers, and synthetic polymer matrices containing polyanhydride, polyorthoester, polyglycolic acid, or a combination thereof (see, for example, U.S. Pat. Nos. 4,846,835; 4,642,120; 5,786,217 and 5,041,138).

Examples of tissues applicable to the techniques of the invention include vascular tissue, skin tissue, hepatic tissue, pancreatic tissue, neuronal tissue, urogenital tissue, gastrointestinal tissue, and musculoskeletal tissue. In addition, the cells in a robust tissue sheet can be genetically modified to express a diagnostic and/or a therapeutic product (e.g., polypeptides or polynucleotides) to generate a genetically engineered tissue graft.

The present invention is also useful in the obtainment of cells from postnatal or adult tissues of patients that present pathologies or disfunctions, for example, genetic or metabolic.

Grafting of scaffolds to an organ or tissue to be regenerated can be performed according to art-recognized methods. The scaffold can be grafted to an organ or tissue of the subject by suturing the graft material to the target organ. The scaffold is also useful for delivery of biologics, enzymes that activate drugs, protease inhibitors, and the like.

In one embodiment, the invention includes the use of the cell extract-based scaffolds of the invention as a platform to direct wound healing and soft tissue repair. The scaffold can be used as a wound dressing or graft for external skin wounds. In a clinical setting, the scaffold can be used to treat wounds resulting from trauma, burns, ulcers, abrasions, lacerations, surgery, or other damage. Surgeons can use these grafts to cover and protect the wound area, to temporarily replace lost or damaged skin tissue, and to guide new tissue generation and wound healing into the damaged area. In a clinical setting, the scaffold may be secured to the wound area using sutures, adhesives, or overlaying bandages. The scaffold may be cut to match the size of the wound, or may overlap the wound edges.

In another aspect of the invention, the scaffold may be tailored for personal/home care by combining the sheet with an adhesive backing to create a scaffold bandage. An adhesive section can hold the scaffold in place on a wounded area and can be removed when the fibers degrade or fuse with the tissue. The scaffold sheet may also be secured with a liquid or gel adhesive.

In another aspect of the invention, scaffold sheets can be used as gauze to absorb fluid and protect large wounds. This scaffold gauze can be wrapped around a wounded area or secured with tape.

In another aspect of the invention, scaffold sheets can be used to treat internal soft tissue wounds such as wounds in the amniotic sac, ulcers in the gastrointestinal tract or mucous membranes, gingival damage or recession, internal surgical incisions or biopsies, etc. The scaffold grafts can be sutured or adhered into place to fill or cover the damaged tissue area.

The choice of material incorporated into the scaffold wound dressings can be determined to match the natural tissue characteristics including mechanical strength and rate of degradation/tissue regeneration. Third, the scaffolds may be embedded or conjugated with various factors which may be released upon degradation. These factors may include, but are not limited to epidermal growth factor (EGF), platelet derived growth factor (PDGF), basic fibroblast growth factor (bFGF), transforming growth factor-β (TGF-β), and tissue inhibitors of metalloproteinases (TIMP), which have been shown to be beneficial in wound healing. Additional wound healing factors such as antibiotics, bacteriocides, fungicides, silver-containing agents, analgesics, and nitric oxide releasing compounds can also be incorporated into the scaffold wound dressings or grafts.

The scaffold may also include agents which promote vascularization or prevent tissue rejection.

Administration of scaffold compositions based on compartmental extracts in accordance with the invention can prevent or treat degenerative conditions related to disease or to normal aging processes.

Scaffolds prepared from extracts isolated primarily from a developing fetal cardiac muscle can be used for adult cardiac regeneration.

Scaffolds prepared from extracts isolated from embryonic stem cells differentiated into bone cells can be used for adult bone regeneration.

Scaffolds prepared from extracts isolated from bone marrow- or fat tissue-derived mesenchymal stem cells differentiated into fat or cartilage cells can be used for adult cartilage and fat tissue reconstruction.

Scaffolds prepared from extracts derived from fetal fibroblasts can be used for connective tissue regeneration, wound healing and tissue augmentation.

The scaffolds can be used in the area of Cardiovascular Surgery, including repair of congenital anomalies (e.g. septal defects), myocardial regeneration (e.g. post-MI, post-traumatic injury), valve repair and replacement, and vascular reconstruction.

The scaffolds can be used in the area of Plastic and reconstructive surgery, including wound healing and skin regeneration, skin substitutes, facial fillers, soft tissue augmentation and reconstruction (e.g. breast).

The scaffolds can be used in the area of Orthopedics, including tendon and ligament repair, bone and cartilage regeneration, and skeletal muscle regeneration.

The scaffolds can be used in the area of Dental surgery, including periodontal defects and dental implants.

The scaffolds can be used in the area of Orthognatic surgery, and General Surgery including gastrointestinal tract reconstruction, ulcer repair, sling procedures, fascia reconstruction (abdominal wall) and prevention of post-operative adhesions.

The scaffolds can be used in the area of Thoracic surgery including upper- and lower airway reconstruction and vocal fold repair.

The scaffolds can be used in the area of Urology and gynecology including bladder reconstruction, urethral reconstruction, urinary incontinence repair and anti-prolapse procedures.

In another aspect, the scaffolds of the invention may also be used for toxicology testing, drug screening, and developing new diagnostic tools and therapeutic strategies.

In another embodiment, the scaffold can include a therapeutic agent. The therapeutic agent can be an anti-tumor agent including but not limited to a chemo therapeutic agent, an anti-cell proliferation agent or any combination thereof.

The invention is not limited to any particular chemotherapeutic agent. For example, any conventional chemotherapeutic agents of the following non-limiting exemplary classes may be incorporated into the scaffold: alkylating agents; nitrosoureas; antimetabolites; antitumor antibiotics; plant alkyloids; taxanes; hormonal agents; and miscellaneous agents.

An anti-cell proliferation agent can further be defined as an apoptosis-inducing agent or a cytotoxic agent. The apoptosis-inducing agent may be a granzyme, a Bcl-2 family member, cytochrome C, a caspase, or a combination thereof. Exemplary granzymes include granzyme A, granzyme B, granzyme C, granzyme D, granzyme E, granzyme F, granzyme G, granzyme H, granzyme I, granzyme J, granzyme K, granzyme L, granzyme M, granzyme N, or a combination thereof. In other specific aspects, the Bcl-2 family member is, for example, Bax, Bak, Bcl-Xs, Bad, Bid, Bik, Hrk, Bok, or a combination thereof. Additional cytotoxic agents include TNF-α, gelonin, Prodigiosin, a ribosome-inhibiting protein (RIP), Pseudomonas exotoxin, Clostridium difficile Toxin B, Helicobacter pylori VacA, Yersinia enterocolitica YopT, Violacein, diethylenetriaminepentaacetic acid, irofulven, Diptheria Toxin, mitogillin, ricin, botulinum toxin, cholera toxin, saporin 6, or a combination thereof.

Scaffold grafts for wound healing may be seeded with cells for faster tissue regeneration and more natural tissue structure. These cells may include, but are not limited to fibroblasts, keratinocytes, epithelial cells, endothelial cells, mesenchymal stem cells, and/or embryonic stem cells.

For further elaboration of general techniques useful in the practice of this invention, the practitioner can refer to standard textbooks and reviews in cell and tissue culture, embryology, and molecular biology. General techniques in cell culture and media collection are outlined in Large Scale Mammalian Cell Culture (Hu at at., Curr. Opin. Biotechnol. 8:148, 1997); Serum-free Media (K. Kitano, Biotechnology 17:73, 1991); Large Scale Mammalian Cell Culture (Curr. Opin. Biotechnol. 2:375, 1991); and Suspension Culture of Mammalian Cells (Birch et al., Bioprocess Technol. 19:251, 1990). Textbooks on the subject include General Techniques in Cell Culture (Harrison & Rae, Cambridge, 1997); Animal Cell Culture Methods (Barnes & Mather, eds., Academic Press, 1998); Culture of Animal Cells (I. Freshney, 4th. ed., John Wiley & Sons, 2000); Guidebook to the Extracellular Matrix, Anchor, and Adhesion Proteins (Kreis & Vale, eds., Oxford, 1999); Handbook of Cellular Manufacturing Systems (S. A. Irani, ed., John Wiley & Sons, 1999). The properties, culture, and differentiation of embryonic stem cells are described in Teratocarci nomas and embryonic stem cells: A practical approach (E J. Robertson, ed., IRL Press Ltd. 1987); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., al., 1993). Differentiation of stem cells is reviewed in Robertson, Meth. Cell Biol. 75:173, 1997; and Pedersen, Reprod. Fertil. Dev. 10:31, 1998. References that further describe the culturing of particular cell types are listed further on in the disclosure.

General biochemical techniques are described in Short Protocols in Molecular Biology (Ausubel et al., eds., 4th ed. 1999). Methods of protein chemistry are described generally in Protein Methods (Bollag et al., 1996); Guide to Protein Purification (Deutscher et al., eds., Methods Enzymol. vol. 182, Academic Press, 1997); Protein Analysis and 5 Purification (L M. Rosenberg, Springer Verlag, 1996).

EXAMPLES

The scaffold of the invention, both in its injectable form and transplantable form, has numerous applications in the medical and surgical field due, in part, to its physical properties, such as biomechanical strength, natural structure, flexibility, suturability, low immunogenicity in comparison to the traditional scaffolds used in the art, and is expected to have an enhanced therapeutic utility for guided tissue regeneration by providing the local cues and structural elements for host cells to migrate, proliferate, differentiate, synthesize their own matrix macromolecules, hence stimulating enhanced tissue regeneration.

Example 1: Culture Device

Figure 1B:
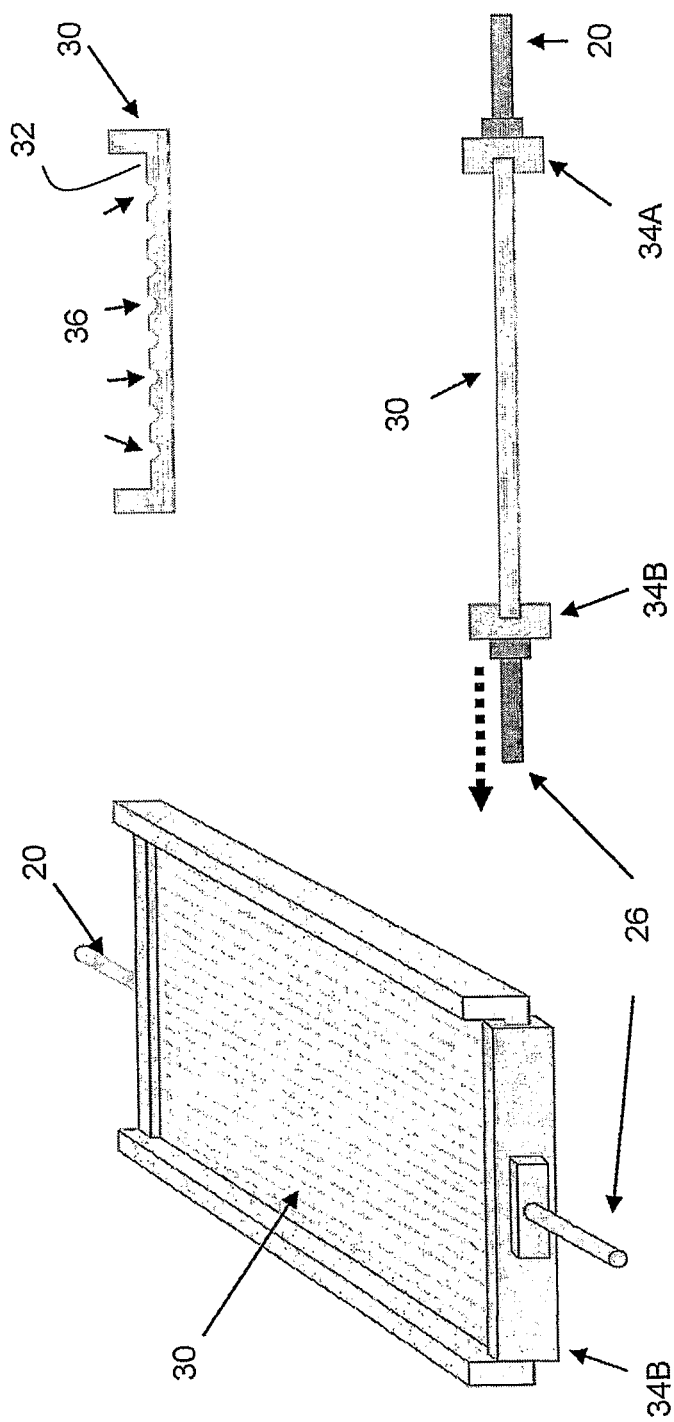

Referring to FIGS. 1A and 1B, there is illustrated an example of a device 10 of the present invention configured and operable for growing cells. The configuration of device 10 is aimed at creating environmental conditions similar to those encountered by cells and tissues in their natural environment inside a living organism. The device is capable of exerting mechanical force onto the cells and to provide a patterned topography of the surface onto which the cells are attached. The combination of mechanical stimulation and nano-scale or micro-scale patterned topography has a significant effect on the organization, orientation, growth, maturation and function of cells and tissues.

The present invention thus provides a novel device capable of exerting mechanical forces and having a patterned surface topography for culturing cells or for generating an engineered tissue. The cells or the engineered tissue cultured in the device may be further used for extraction of cellular components for preparing the scaffolds of the invention.

As shown in FIG. 1A, device 10 comprises a culture chamber 12, which is installed in an incubator 14 and is associated with a control system 16. Typically provided in the incubator 14 is a load cell 18 equipped with a fixed shaft 20.

Culture chamber 12 is configured for supporting the cells during culturing. Typically, culture chamber defines a support unit, which is shown more specifically in FIG. 1B being generally denoted 30. Support unit 30 has a flexible support surface 32, where cells are initially seeded, and grip mechanisms 34A and 34B at opposite ends thereof. Support surface 32 is made of a flexible material, for example, a polymer or a copolymer exhibiting rubber-like or elastic properties, alone or in combination with other natural or synthetic materials the selection of which would be within the ability of one skilled in the art. The flexible material may be combined with other materials to control the adhesive properties of the surface. In a preferred embodiment the flexible material is silicone. Support surface 32 may be constituted by the bottom surface of culture chamber 12. Support surface 32 may be detached from the culture unit. Grip mechanism 34A is coupled to fixed shaft 20 of the loading cell 18. Grip mechanism 34B is associated with a mechanical drive system 22.

Drive system 22 comprises a linear motor 24 equipped with a moving shaft 26. Generally, the drive system is configured to cause appropriate stress onto the growing cells and tissues by applying thereto appropriate mechanical forces. To this end, moving shaft 26 is coupled to grip mechanism 34B. Drive system operates to induce uniaxial tensile strain lengthwise to the surface 32. Mechanical forces play an important role in the organization, growth, maturation, and function of living tissues. Mechanical stimulation may be used to induce cellular orientation and phenotypic modulation of cultured cells. Thus, appropriate forces can be applied to growing cells and tissues in order to induce fiber and cell orientation, extracellular matrix maturation and tissue organization.

As further shown in FIG. 1B, support surface 32 of the support unit has a certain pattern (surface relief) which may be periodical or random. Such a surface relief is in the form of spaced-apart pits or grooves 36. This may for example be achieved by providing the silicone support unit 30 with micro-fabricated flexible grooved surface 32. The grooves may be oriented at any direction, or at any micro-fabrication pattern. Preferably, the grooves are oriented lengthwise. The grooves can for example be of about 5-20 µm deep, 5-20 µm wide, and spaced a 5-20 µm distance from one another. The grooves can also be at a nanoscale.

A patterned support surface creates a surface topography that presents a template for the growing cells. Topographical features of a surface have a significant effect on cellular behavior and orientation.

Turning back to FIG. 1A, control system 16 is typically a computer system including inter alia a processor utility 16A (controller and data acquisition), a data presentation utility (monitor) 16B, an analog and digital front end utility 16C, etc. Control system 16 operates the load cell unit 20 and mechanical drive system 22, and runs an appropriate algorithm enabling variation of the strain programs.

The controllably operable mechanical drive system defines a straining system. Such straining system is formed by linear motor 24, load cell 18 and control system 16 (i.e. analog front end utility 16C of the processor 16B). It should be noted that generally the mechanical movement of the flexible template surface can be implemented manually. Preferably, however, the staining system applies predefined strain with a predefined loading program and predefined training sets to the culture unit.

In the present invention, the cell culture chamber 12 is used as a platform to transfer the uniaxial strain stimulus to the cell culture. The chamber can be sterilized; connected to the linear motor outside incubator using a shaft; connected to the load cell using a shaft; and varying cell ledges can be used on two hinges inside the chamber.

The control system 16 may perform a training set control; allows control over all training parameters and programs. The training program parameters may be saved and may be displayed. Sensors and motor state can be displayed at all time, on time base graph. When required, sensor and motor state may be recorded. Data may be saved and exported for later analysis in any suitable standard format.

Table 1 presents an example of the elements and their operational characteristics suitable to be used for the components of the above described straining system.

TABLE 1

| Component | Description | Spec. |
|---|---|---|
| Linear Motor | Uniaxial linear motor | |
| Load Cell | Force sensor | Resolution 0.02 mN |
| | | Active Range 0-100 mN |
| Analog and Digital Front End | Amplify and filter sensors signals before ADC Motor driver using DAC control Optional I/O | |
| Controller and Data Acquisition | CPU (optional if real time required) ADC DAC I/O | 12 bit 8 analog IN 2 analog OUT 8 I/O ports |
| Monitoring System | Recording Data from sensors and motor Controlling motor | |

The straining system can be used to apply stimulation on cell culture with predefined training sets. The latter may include ramp and hold training set, and/or sine training set, and/or ramp and hold and sine modulation training set. The latter is a modulation of Ramp&Hold set with a sine set to result with complex training set.

Figure 2:
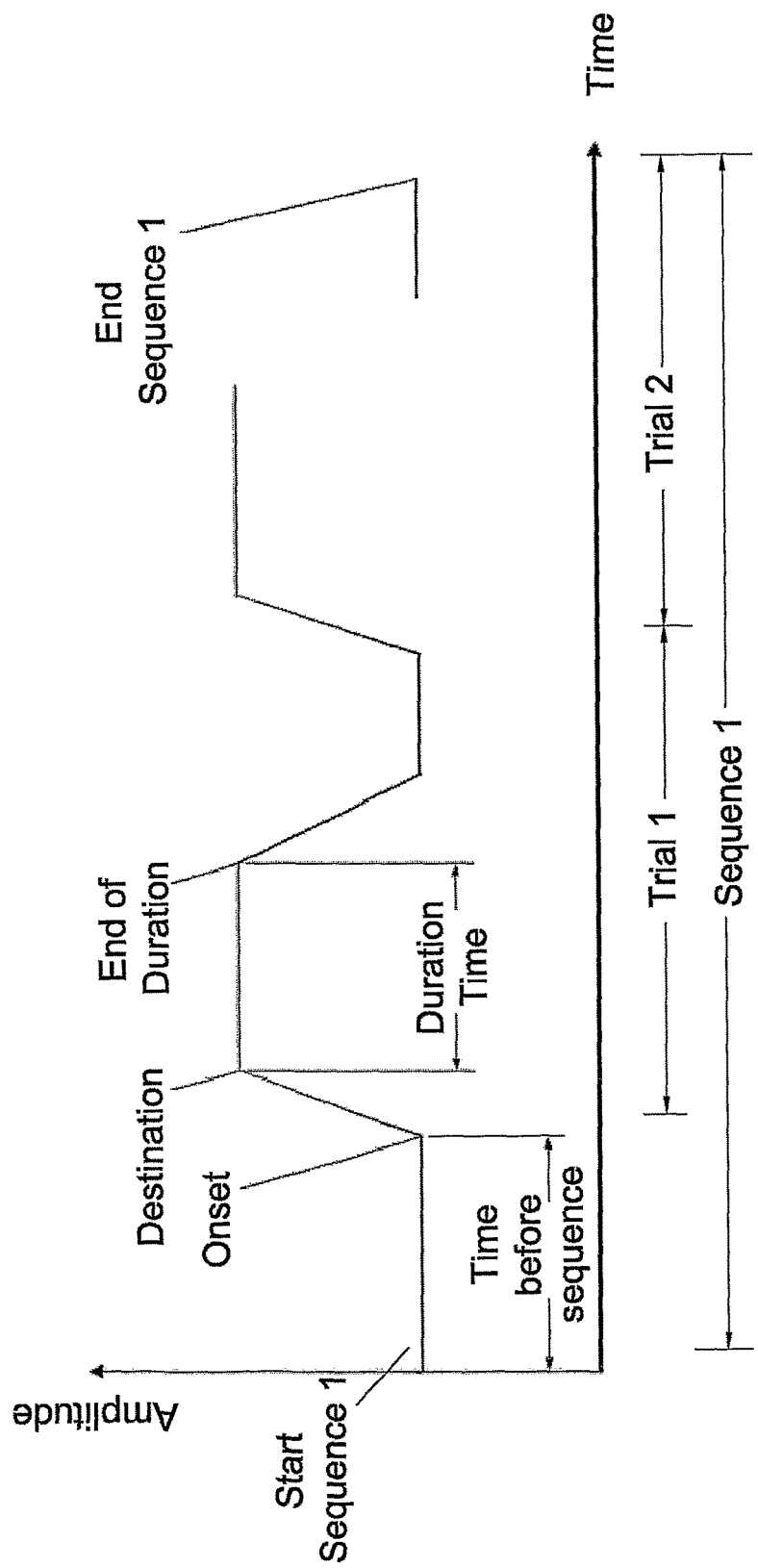
FIG. 2 is a schematic representation of an application of a ramp and hold training set.

FIG. 2 exemplifies, in a self-explanatory manner, application of a ramp and hold training set.

Table 2 and 3 below describe the parameters involved in the application of respectively ramp and hold training set and sine training set.

TABLE 2

| Parameter | Description | Optional Spec. |
|---|---|---|
| Test | A set of sequences with different training sets | |
| Sequence | A set of trails of training sets. A sequence may be repeated during a test. | |
| Trail | One cycle of training set. A trail may be repeated during a sequence. | |
| Baseline | The training set stimulation start value. Stimulation will be applied around baseline. | |
| Stimulation | Amplitude of stimulation Distance Strain Force *compressing may be applied as well | Distance-x1 → x1 Strain-σ1 → σ1(optional) Force-F1 → F1(optional) |
| Duty Cycle | Duration Time The time in a cycle which strain, distance or force are applied | 1. Percentage 1.1. 0-100% of cycle 1.2. 0.1% resolution 2. Time 2.1. 0-inf 2.2. 0.1 sec resolution |
| Frequency | Onset to Onset The frequency of applied stimulation. | 1. Frequency 1.1. 0-10 Hz. 1.2. 0.1 Hz resolution. 2. Time |
| Rate | Amplitude change rate from Onset to destination and from destination to base level. | 1. Amplitude/sec 2. % of duration |
| Trail | Each trail contain set of parameters and can be repeated | |
| Sequence | Each sequence is composed of few trails | |

TABLE 3

| Parameter | Description | Optional Spec. |
|---|---|---|
| Test | A set of sequences with different training sets | |
| Sequence | A set of trails of training sets. A sequence may be repeated during a test. | |
| Trail | One cycle of training set. A trail may be repeated during a sequence. | |
| Baseline | The training set stimulation start value. Stimulation will be applied around baseline. | |
| Stimulation | Amplitude of stimulation Distance Strain Force | Distance-x1 → x1 Strain-σ1 → σ1 (optional) Force-F1 → F1 (optional) |
| Frequency | The frequency of applied sine stimulation. | 1. Frequency |
| Trail | Each trail contain set of parameters and can be repeated | |
| Sequence | Each sequence is composed of few trails | |

The following are some specific but not limiting examples for the training sets: (1) Constant strain of value ε for t duration; (2) Cycle of constant strain of value ε1 for t1 duration, then constant strain of value ε1 for t3 duration; (3) Cyclic R&H strain of value ε for t duration; (4) Constant strain of value ε1 for t1 duration with R&H strain modulation.

As indicated above, the culture unit 12 of the device 10 is located inside a tissue culture incubator 14. By making a housing of the culture unit 12 from a non-adherent material or a material that cells bind to only weakly, such as stainless steel or ePTFE, the culture unit can be removed from the incubator without damaging the tissue sheet (support surface 32). In other applications, it is conceivable that stronger adhesion would be desirable in which case different materials, such as treated polystyrene, are used. In yet other applications of the technology biodegradable materials may be desirable including, for example, polylactic acid, polyglycolic acid, collagen based material, cat gut sutures, and the like. Typically the culture unit 12 is substantially non-porous or completely non-porous thereby making it easier to remove the culture unit when needed.

The culture unit is made from any material that does not interfere with the development or differentiation of cells, such as stainless steel. Magnets or metal ingots coated with Teflon or any polymer material known in the art to be compatible with tissue culture may also be used.

The device (culture unit) according to the current invention may be covered with thermoresponsive polymers such as those used with dishes supplied by CellSeed, Inc. (Tokyo, Japan).

Typically the device (culture unit) will be comprised of a material that can be sterilized by conventional techniques such as heat, ethylene oxide, or gamma sterilization. The device should be of a biocompatible material in order to prevent cytotoxic effects upon cells. Depending upon the desired culture conditions, tissue construct to be made, and cell types present, the device may be made of either a biodegradable or a non-biodegradable material. For example, where the tissue construct comprises a three-dimensional structure that prevents easy removal of the device or removal of the device would result in undesirable damage to a tissue sheet then the tissue manipulation devices should be made of a biodegradable material.

A compressive force normal to the plane of a sheet of tissue enhances fusion between adjacent layers of sheets of tissue. Compression improves contact between layers of tissue and encourages fusion of the layers of tissue.

Example 2: Preparing a Transplantable Scaffold for Skin Tissue Engineering

Materials and Methods

Culturing of Dermal Fibroblasts

Adult normal human dermal fibroblasts are purchased from Lonza (Clonetics-NHDF-Ad Cat. Cc-2511, Lonza, Basel, Switzerland) and are propagated in fibroblast growth medium (FGM; Lonza) containing 10% fetal bovine serum (FBS; Lonza). The cells are maintained at 37° C. in a 5% CO2 incubator.

Alternatively, dermal fibroblasts are isolated from skin samples using the following method:

Samples of foreskins obtained from new-born boys are cut to a size of about 5×5 mm, washed twice in PBS, rinsed in 70% ethanol, and washed again twice in PBS. Then the samples are treated with Dispase (Gibco) overnight at 4° C. The epidermis is then stripped off, and the dermis is treated with 0.25% trypsin (Sigma) at 37° C. Trypsin inhibitor is used to stop the digestion. The resulting dermal cells are centrifuged at approximately 500 g for 5 minutes and suspended in complete Dulbecco's modified Eagle's medium (DMEM) with 10% fetal bovine serum (FBS), 100 units/ml penicillin, and 100 mg/ml streptomycin. Cell number and viability is determined using trypan blue. Cells are seeded at a density of $3 \times 10^4$ cells/cm$^2$ on T75 tissue culture flasks. Culture medium is changed every 3-4 days. When cells reach 90% confluence, they are passaged in a ratio of 1:3. Cells are resuspended in a 10% DMSO cryopreservation solution and cryopreserved in liquid nitrogen, or immediately used.

Culturing of Epidermal Keratinocytes

Adult normal human epidermal keratinocytes are purchased from Lonza (Clonetics-NHEK-Ad Cat. Cc-2501, Lonza, Basel, Switzerland) and are propagated in chemically defined keratinocyte growth medium (KGM-CD; Lonza). The cells are maintained at 37° C. in a 5% CO2 incubator.

Alternatively, epidermal keratinocytes are isolated from skin samples using the following method:

Skin sample is obtained from mammoplasties, abdominal skin, cadaver skin, and preferably from foreskin. The skin sample is rinsed extensively with PBS containing 100 U/ml penicillin, and 100 mg/ml streptomycin, and then cut into pieces of approximately 0.5×0.5 cm, and incubated overnight at 4° C. in a solution containing 25 U/ml dispase in order to obtain separation of epidermis and dermis. The epidermis is removed from the dermis by using forceps, and further processed by incubation for 30 minutes at 37° C. in a solution containing 0.05% trypsin and 0.02% EDTA. The epidermis is then suspended by up-and-down pipetting and passaging through an injection needle to obtain single cell suspension. The trypsin is then neutralized by adding a trypsin inhibitor, and the cells are filtered through sterile gauze, and centrifuged at approximately 200 g for 5 minutes and suspended in complete Dulbecco's modified Eagle's medium (DMEM) with 10% fetal bovine serum (FBS), 100 units/ml penicillin, and 100 mg/ml streptomycin. Cell number and viability is determined using trypan blue. Cells are seeded at a density of $3 \times 10^4$ cells/cm$^2$ on T75 tissue culture flasks. Culture medium is changed every 3-4 days. When cells reach 90% confluence, they are passaged in a ratio of 1:3. Cells are resuspended in a 10% DMSO cryopreservation solution and cryopreserved in liquid nitrogen, or immediately used.

Culturing of Bone Marrow Derived Mesencymal Stem Cells

Human Mesenchymal Stem Cells are purchased from Lonza (Poetics Cat. PT-2501, Lonza, Basel, Switzerland) and are propagated in Mesenchymal Stem Cell growth medium (MSCGM; Lonza). The cells are maintained at 37° C. in a 5% CO2 incubator. The cells are seeded at 5,000 cells per cm$^2$ in T-flask, expanded for 3 to 4 days and at 70% confluency, harvested with trypsin, collected, and centrifuged at 300 rcf (relative centrifugal force) for 5 minutes. The trypsin/media are removed by aspiration and cells are washed three times with phosphate buffered saline (PBS).

Alternatively, mesenchymal stem cells are isolated from bone marrow samples using the following method:

Bone marrow aspirate is obtained from the iliac crest of normal donors. The sample is transferred to a 50 ml sterile tube and supplemented with 20 ml of Hank's saline solution at +4° C. The tube is centrifuged at approximately 1000 rpm for 5 minutes to pellet the cells and to eliminate the supernatant and the lipid layer, which are then aspirated. Then the pellet is loaded onto Percoll or Ficoll type gradients (Sigma), centrifuged at 500 g for 15 minutes, after which the upper, low-density cell fraction containing mesenchymal cells is collected and plated for further expansion. Cells are cultured in alpha-MEM medium supplemented with 10% fetal bovine serum and 100 units/ml penicillin/streptomycin at 37° C. in humidified atmosphere containing 95% air and 5% CO2. After one day, nonadherent cells are removed from the cultures by replacing the original medium with fresh medium. Subsequent medium changes are performed every 3-5 days. When culture dishes become confluent, the cells are detached using 0.25% trypsin containing 0.1 mM EDTA (GIBCO) for 10-15 minutes at 37° C. The action of trypsin is stopped with ½ volume fetal bovine serum. The cells are counted, split 1:3, and replated. Cells are resuspended in a 10% DMSO cryopreservation solution and cryopreserved in liquid nitrogen, or immediately used.

Step 1: Seeding Dermal Fibroblasts on a Cell Culture Device and Engineering a Dermal Sheet In order to facilitate extracellular matrix formation and induce alignment of cells and provide mechanical cues, cells are seeded and grown on a device designed to recapitulate some of the native micro-environmental cues required for the growing of cells and formation of tissues. Details of an exemplary device are provided in Example 1 above.

Cultured dermal fibroblasts are harvested using 0.25% trypsin-EDTA to detach the cells from the culture plates. Trypsin is subsequently neutralized with growth medium. Cells are then pelleted at approximately 500 g, resuspended in fresh growth medium, counted with a hemocytometer, seeded onto the silicone substrate of the culture device at a density of $5 \times 10^4$ cells/cm$^2$. After incubation of 20-40 minutes allowing cells to attach, a pre-defined training program is initiated to apply a uniform cyclic strain of 2-4%, at a 0.2 Hz frequency. Culture medium is changed every 3-4 days. Following a period of approximately two weeks (time may change between different types of dermal fibroblasts) a layer of dermal sheet is formed and the training program is stopped. Tissue formation is verified by histological analysis, and by using scanning electron microscopy imaging.

Step 2: Isolation of Extracellular Compartment

The silicone culture substrate with the grown layer of dermal fibroblast sheet are transferred to a sterile hood and washed in PBS containing a protease inhibitor cocktail (Sigma) for 30 minutes with agitation, then incubated with agitation in 0.3% sodium dodecyl sulphate (SDS) in a Tris buffer for 12-24 hours at room temperature, then washed in PBS for 10 minutes with agitation. The wash is repeated three times. The resultant ECM sheet is freeze-dried and stored at room temperature or immediately used for the next step.

Step 3: Redesigning

Cultured epidermal keratinocytes are harvested using 0.25% trypsin-EDTA to detach the cells from the culture plates, which is subsequently neutralized with growth medium. Then cells are pelleted at approximately 200 g, resuspended in fresh growth medium, counted with a hemocytometer and seeded on the dermal ECM at a density of $5 \times 10^4$ cells/cm$^2$. The resultant keratinocyte-seeded dermal ECM sheet still attached to the silicone culture substrate is transferred back to the incubator and cultured at 37° C. in a 5% CO2, subjected to the training program used in step 2 to apply a uniform cyclic strain of 2-4%, at a 0.2 Hz frequency. Culture is maintained for duration of 7-10 days. Culture medium is changed every 3-4 days. Evaluation of adherence and distribution of seeded cells is done by histological analysis and scanning electron microscopy imaging.

Step 4: Elimination of Seeded Cells

The silicone culture substrate with the seeded sheet are transferred to a sterile hood and washed in PBS containing protease inhibitor cocktail (Sigma) for 30 minutes with agitation, then incubated with agitation in 0.3% sodium dodecyl sulphate (SDS) in a Tris buffer for 12-24 hours at room temperature, then washed in PBS for 10 minutes with agitation for three times. Verification of cell removal and evaluation of the redesigned scaffold is done by histological analysis, scanning electron microscopy imaging and by SDS-PAGE and Western blotting.

Step 5: Storage and Handling

The redesigned scaffold resulting from step 4 is removed from the sterile washing solution and then gently stretched until it is flat and then placed on a drying platform. Any drying apparatus may be used that is suitable for drying scaffold material. Preferably, however, the scaffold is placed inside a drying bag (Tyvek), transferred to a freeze-drier. Handling at any stage is done under sterile conditions. Following drying, the scaffold is stored at above freezing temperature, preferably 0-4° C., sealed in a light-protected environment, at any container suitable for long-term storage.

Step 6: Using the Scaffold for Skin Regeneration

After removal from the packaging, the scaffold in its dry state is trimmed prior to use, and cut into the exact size needed, for example 3 cm×5 cm. The scaffold is hydrated with a sterile physiological solution such as sterile 0.9% NaCl solution. Rehydration is done in a dish or preferably while on the surgical site.

The scaffold is used for example to treat skin wounds or skin loss by placing the scaffold directly over the area of the wound or skin loss. Then the scaffold is sutured effectively and covered with sterile wound dressing material.

Example 3: Preparing a Transplantable Scaffold Using Two Cell Types in the Redesigning Step Bone marrow derived mesenchymal stem cells are used as demonstrated in step 1 in Example 2 above, to form a mesenchymal sheet. Then the extracellular compartment is isolated (see step 2). Then redesigning is done by seeding firstly dermal fibroblasts, followed by cell elimination, then a second step of redesigning is done by seeding epidermal keratinocutes, followed by a second step of cell elimination. Alternatively, the two cell populations are mixed prior to seeding and seeded simultaneously.

Example 4: Preparing an Injectable Scaffold for Skin Tissue Engineering

Materials and Methods

Preparation of Intracellular Extracts

Intracellular extracts are prepared as described in WO 02/057415. Cultured cells are harvested using standard methods and washed by centrifugation at 500 g for 10 minutes in a 10 ml conical tube at 4° C. The supernatant is discarded, and the cell pellet is resuspended in a total volume of 50 ml of cold PBS. The cells are centrifuged at 500 g for 10 minutes at 4° C. This washing step is repeated, and the cell pellet is resuspended in approximately 20 volumes of ice-cold interphase cell lysis buffer (20 mM Hepes, pH 8.2, 5 mM MgCl$_2$, 1 mM DTT, 10 pM aprotinin, 10 pM leupeptin, 10 pM pepstatin A, 10 pM soybean trypsin inhibitor, 100 pM PMSF, and optionally 20 pg/ml cytochalasin B). The cells are sedimented by centrifugation at 800 g for 10 minutes at 4° C. The supernatant is discarded, and the cell pellet is carefully resuspended in no more than one volume of interphase cell lysis buffer. The cells are incubated on ice for one hour to allow swelling of the cells. The cells are then lysed by either sonication using a tip sonicator or Dounce homogenization using a glass mortar and pestle. Cell lysis is performed until at least 90% of the cells and nuclei are lysed, which may be assessed using phase contrast microscopy. Duration and power of sonication required to lyse at least 90% of the cells and nuclei may vary depending on the type of cell used to prepare the extract.

The cell lysate is placed in a 1.5-ml centrifuge tube and centrifuged at 10,000 to 15,000 g for 15 minutes at 4° C. using a table top centrifuge.

The tubes are removed from the centrifuge and immediately placed on ice.

The supernatant is carefully collected using a 200 µl pipette tip, and the supernatant from several tubes is pooled and placed on ice. This supernatant is the cytoplasmic extract. This cell extract may be aliquoted into 20 pl volumes of extract per tube on ice and immediately flash-frozen on liquid nitrogen and stored at 80° C. until use.

Alternatively, the cell extract is placed in an ultracentrifuge tube on ice (e.g., fitted for an SW55 Ti rotor; Beckman). If necessary, the tube is overlayed with mineral oil to the top. The extract is centrifuged at 200,000 g for three hours at 4° C. to sediment membrane vesicles contained in the cytoplasmic extract. At the end of centrifugation, the oil is discarded. The supernatant is carefully collected, pooled if necessary, and placed in a cold 1.5 ml tube on ice. This supernatant is the cytosolic extract. The extract is aliquoted and frozen as described for the cytoplasmic extract.

Isolation of Cell Nuclei and Preparation of Nuclear Extract

Cells are harvested in PBS using standard procedures, and several washing steps are performed to transfer the cells from their original media into a hypotonic buffer (10 mM Hepes, pH 7.5, 2 mM MgCl$_2$, 25 mM KCl, 1 mM DTT, 10 pM aprotinin, 10 pM leupeptin, 10 pM pepstatin A, 10 pM soybean trypsin inhibitor, and 100 pM PMSF). For example, the cells may be washed with 50 ml of PBS and pelleted by centrifugation at 500 g for 10 minutes at 4° C. The PBS supernatant is decanted, and the pelleted cells are resuspended in 50 ml of PBS and centrifuged, as described above. After this centrifugation, the pelleted cells are resuspended in 20-50 volumes of ice-cold hypotonic buffer and centrifuged at 500 g for 10 minutes at 4° C. The supernatant is again discarded and approximately 20 volumes of hypotonic buffer are added to the cell pellet. The cells are carefully resuspended in this buffer and incubated on ice for at least one hour, resulting in the gradual swelling of the cells.

To allow isolation of the nuclei from the cells, the cells are lysed using standard procedures. For example, 2-5 ml of the cell suspension may be transferred to a glass homogenizer and Dounce homogenized using an initial 10-20 strokes of a tight-fitting pestle. Alternatively, the cell suspension is homogenized using a motorized mixer (e.g., Ultraturrax). If desired, cell lysis may be monitored using phase contrast microscopy at 40-fold magnification. During this homogenization, the nuclei should remain intact and most or preferably all of the originally attached cytoplasmic components such as vesicles, organelles, and proteins should be released from the nuclei. If necessary, 1-20 μg/ml of the cytoskeletal inhibitors, cytochalasin B or cytochalasin D, may be added to the aforementioned hypotonic buffer to facilitate this process.

Homogenization is continued as long as necessary to lyse the cells and separate cytoplasmic components from the nuclei. For some cell types as many as 100, 150, or more strokes may be required. The lysate is then transferred into a 15 ml conical tube on ice, and the cell lysis procedure is repeated with the remainder of the suspension of swollen cells. Sucrose from a 2M stock solution made in hypotonic buffer is added to the cell lysate, resulting in a final concentration of 250 mM sucrose. This solution is mixed by inversion, and the nuclei are pelleted by centrifugation at 400 g in a swing out rotor for 10 to 40 minutes at 4° C. The supernatant is then discarded, and the pelleted nuclei are resuspended in 10-20 volumes of nuclear buffer (10 mM Hepes, pH 7.5, 2 mM $MgCl_2$, 250 mM sucrose, 25 mM KCl, 1 mM DTT, 10 pM aprotinin, 10 pM leupeptin, 10 pM pepstatin A, 10 pM soybean trypsin inhibitor, and 100 pM PMSF). The nuclei are sedimented and resuspended in 1-2 volumes of nuclear buffer, as described above. The freshly isolated nuclei may either be used immediately for extract preparation or stored for future use. For storage, the nuclei are diluted in nuclear buffer to a concentration of approximately $10^6$/ml. Glycerol (2.4 volumes of 100% glycerol) is added and mixed well by gentle pipetting. The suspension is aliquoted into 100-500 all volumes in 1.5-ml tubes on ice, immediately frozen in a methanol-dry ice bath, and stored at −80° C. Prior to use, aliquots of the nuclei are thawed on ice or at room temperature. One volume of ice-cold nuclear buffer is added, and the solution is centrifuged at 1,000 g for 15 minutes in a swing out rotor. The pelleted nuclei are resuspended in 100-500 μl nuclear-buffer and centrifuged as described above. The pelleted nuclei are then resuspended in a minimal volume of nuclear buffer and stored on ice until use.

Preparation of Nuclear Extract: the Nuclei are Lysed by Either Sonication Using a tip sonicator or Dounce homogenization using a glass mortar and pestle. Duration and power of sonication required may vary depending on the type of cell used to prepare the extract. The nuclear extract is derived by a 10-60 minute incubation in nuclear buffer containing NaCl or KCl at a concentration of 0.15-800 mM under agitation. The lysate is centrifuged to sediment unextractable components. The supernatant containing the extract is dialyzed to eliminate the NaCl or KCl. The dialyzed nuclear extract is aliquoted and stored frozen.

Combination of Cell Extract with Nuclear Extract

If desired, cell extract can be enriched with additional nuclear factors. Nuclei are purified for example from cells of the cell type from which the extract is derived and nuclear extract is prepared as described above. The nuclear extract is added at various concentrations to the whole cell extract described above.

Step 1: Seeding Dermal Fibroblasts on a Culture Device

Cultured dermal fibroblasts are harvested using 0.25% trypsin-EDTA to detach the cells from the culture plates, which is subsequently neutralised with growth medium. Then cells are pelleted at approximately 500 g, resuspended in fresh growth medium, counted with a hemocytometer seeded onto the silicone substrate of the culture device at a density of $2\times10^3$ cells/$cm^2$. After incubation of 30-40 minutes, a pre-defined training program is initiated to apply a uniform cyclic strain of 2-4%, at a 0.2 Hz frequency. When the culture reaches approximately 50-60% confluency, the training program is stopped and cells are harvested in their exponential growth phase to benefit from maximal transcriptional activity. Tissue formation is verified by histological analysis, and by using scanning electron microscopy imaging.

Step 2: Isolation of Intracellular Compartment

The cytoplasmic compartment of the dermal fibroblasts is extracted using the method described above.

Step 3: Fabrication of Transplantable Scaffold Using Electro-Spinning

The dermal cytoplasmic extract is lyophilized in a lyophilizer for 2 days. Then the lyophilized extract is dissolved in 1,1,1,3,3,3 Hexafluoro-2-Propanol (HFP) (Sigma). The Extract solution is left to stir at least 24 hours or in a ~50° C. water-bath for overnight before electrospinning, to ensure complete dissolution. The supernatant is collected for electrospinning.

Fibers are electrospun by using a syringe pump (Fisher) to eject solution from a 3 ml syringe through an 18-gauge needle at a delivery rate of 0.5-1.0 ml/h, an air gap distance of 10-15 cm, and accelerating voltage of 12-20 kV. Fibers are collected onto an aluminum collector. For measurement of fiber diameters, glass coverslips coated with electrospun fibers are mounted onto metal stubs with carbon tape and sputter-coated for 30 sec with platinum and palladium prior to visualization in an environmental scanning electron microscope.

Step 4: Redesigning

Cultured epidermal keratinocytes are harvested using 0.25% trypsin-EDTA to detach the cells from the culture plates, which is subsequently neutralized with growth medium. Then cells are pelleted at approximately 200 g, resuspended in fresh growth medium, counted with a hemocytometer and seeded on the electro-spun dermal scaffold at a density of $5\times10^4$ cells/$cm^2$. After incubation of 20-40 minutes allowing cells to attach, the resultant keratinocyte-seeded dermal scaffold is loaded onto the device to induce additional mechanical strain, and incubated at 37° C., 5% CO2. Culture is maintained for 7-10 days. Culture medium is changed every 3-4 days.

Step 5: Elimination of Seeded Cells

The keratinocyte-seeded dermal scaffold is transferred to a sterile hood and washed in PBS containing a protease inhibitor cocktail (Sigma) for 30 minutes with agitation, then incubated with agitation in 0.3% sodium dodecyl sulphate (SDS) in a Tris buffer for 12-24 hours at room temperature, then washed in PBS for 10 minutes with agitation for three times. Verification of cell elimination is done using fluorescence microscopy and scanning electron microscopy imaging.

Step 6: Handling the Scaffold

The redesigned scaffold resulting from step 5 is removed from the sterile washing solution and then gently stretched until it is flat and then placed on a drying platform. Any drying apparatus may be used that is suitable for drying scaffold material. Preferably, however, the scaffold is placed inside a drying bag (Tyvek), transferred to a freeze-drier. Handling at any stage is done under sterile conditions. Following drying, the scaffold is cut manually using a scalpel, or fragmented using a freezer mill, and then solubilized or suspended with a gel compound and formulated into a hydrophilic gel.

Step 7: Using the Scaffold for Skin Regeneration

The scaffold formulated into a gel can be applied topically on burn wounds or skin ulcers. The scaffold can be applied with any pharmaceutically acceptable carrier other than a gel such as a cream or an ointment.

Example 5: Preparation of a Combined Injectable Scaffold for Skin Tissue Engineering Materials and Methods Cell Cycle Phase Synchronization (Performed Prior to Extraction of Intracellular Compartments)

For extract preparation the cell populations may be synchronized naturally or chemically. Cells may be arrested in any phase of the cell cycle, such as G0, interphase and mitosis, using standard procedures.

Cells may be incubated, for example, in low serum, such as 5%, 2%, or 0% serum, for 1, 2, 3, or more days to increase the percentage of cells in G0 phase. To synchronize cells in G1, the cells may be grown to confluence as attached cells and then incubated in 0.5-1 µg/ml nocodazole (Sigma Chemicals, St. Louis, Mo.) for 17-20 hours. The flasks containing the attached cells are shaken vigorously by repeatedly tapping the flasks with one hand, resulting in the detachment of mitotic cells and G1 phase doublets. The G1 phase doublets are pairs of elongated cells at the end of the division process that are still connected by a thin bridge. Detached G1 phase doublets may be isolated from the media based on this characteristic doublet structure. The G1 phase doublets may remain attached or may divide into two separate cells after isolation.

To increase the percentage of cells in S phase, the cells may be cultured in the presence of aphidicolin which inhibits DNA polymerase and thus inhibits DNA synthesis and arrests cells in S phase.

Alternatively, cells may be incubated in the presence of excess thymidine. The resulting high intracellular concentration of thymidine relative to that of other nucleotides also inhibits DNA polymerase.

Cells may be synchronized in G2 by incubating the cells in the presence of aphidicolin to arrest them in S phase and then washing the cells three times by repeated centrifugation and resuspension in phosphate buffered saline (PBS), as described herein. The cells are then incubated for a length of time sufficient for cells to enter G2 phase. For example, cells with a doubling time of approximately 24 hours, may be incubated for between 6 and 12 hours to allow them to enter G2 phase. For cells with shorter or longer doubling times, the incubation time may be adjusted accordingly.

Cells may be synchronized in mitosis by incubating them in 0.5 µm/ml nocodazole for 17-20 hours, and the mitotic cells are detached by vigorous shaking, as described above. The detached G1 phase doublets may be discarded, or they may be allowed to remain with the mitotic cells which constitute the majority (over 80%) of the detached cells. The harvested detached cells are centrifuged at 500 g for 10 minutes in a 10 ml conical tube at 4° C.

Preparation of Whole Intracellular Extracts

The cultured cells are rinsed 3-4 times with PBS, and culture medium, such as alpha-MEM or DMEM/F12 (Gibco) is added without additives or serum. 12-24 hours later, the cells are washed twice with PBS and harvested, preferably scraped with a rubber policeman and collected in a 50 ml Falcon tube (Becton Dickinson). Then cells are washed and resuspended in ice-cold cell lysis buffer (20 mM HEPES, pH 8.2, 50 mM NaCl, 5 mM $MgCl_2$, 1 mM dithiothreitol and a protease inhibitor cocktail), sedimented at 400 g and resuspended in one volume of cell lysis buffer. Cells are sonicated on ice in 200 µl aliquots using a sonicator fitted with a 2-mm diameter probe until all cells and nuclei are lysed, as can be judged by phase contrast microscopy. The lysate is centrifuged at 10,000-14,000 g, 15-30 minutes at 4° C. to pellet the coarse material and any potentially remaining non-lysed cell. The supernatant is aliquoted, frozen and stored in liquid nitrogen or immediately used. Protein concentration of the extract is analyzed by Bradford assay, pH is adjusted to around 7.0±0.4 and oslolarity is adjusted to ~300 mOsm prior to use, in necessary, (by diluting with water).

Preparation of Tissue Extract:

Tissue preparation can be performed by any method known in the art, for example, see U.S. Pat. No. 4,829,000.

A tissue specimen is weighed and trimmed. The specimen is then washed and homogenized in ice cold 3.4M NaCl buffer supplemented with a protease inhibitor cocktail (0.5 mM PMSF, 2 mM EDTA, 0.1M EACA, 2 mM NEM and the like). The homogenate is then centrifuged at 10,000 rpm at 4° C. for 15 minutes, following which the supernatant is discarded and pellets are resuspended in the 3.4M NaCl buffer. This step is repeated 2-3 times. Pellets are then resuspended in a 2M urea buffer, homogenized and stirred overnight at 4° C. Then the extract is centrifuged at 14,000 RPM at 4° C. for 30 minutes and the supernatant is reserved. Pellets are re-homogenized in half the original volume of 2M urea buffer then the centrifugation step is repeated. The supernatant is then combined with the previously reserved supernatant. Then the combined extract is dialyzed in 0.05 M Tris-saline buffer with chloroform (for sterilization) for two hrs in 4° C. then it is dialyzed in Tris-saline buffer several times, followed by DMEM. Then the extract is aliquoted into sterile tubes and stored in liquid nitrogen, or immediately used.

Step 1: Isolation of Placental Tissue Extract

Placenta is obtained following full term or pre-term deliveries, transported to the laboratory, and processed under aseptic conditions. The placenta is placed in a sterile container, and the umbilical cord is cut off the placental disc. The amniotic membrane is separated from the chorion, removed, and roughly chopped. Then the tissue samples are further processed according to the method described above for isolation of tissue extract.

Step 2: Isolation of Dermal Fibroblast Whole Intracellular Extract

Dermal fibroblasts are harvested from the culture device described in example 1 in their exponential growth phase when the culture reaches approximately 50-60% confluency. Then the cells are synchronized in the desired cell cycle phase, such as in mitosis, according to the method described above. Then the synchronized cells are harvested, and the whole intracellular compartment is extracted using the method described above, and then added at various concentrations to the placental tissue extract described in step 1.

Step 3: Isolation of Nuclear Extract from Synchronized Epidermal Keratinocytes

Epidermal keratinocytes are harvested from the culture device described in example 1 in their exponential growth phase when the culture reaches approximately 50-60% confluency. Then the cells are synchronized in the desired cell cycle phase, such as in G1 phase, according to the method described above. Then the synchronized cells are harvested and the nuclear compartment is extracted according to the method described above, and then added at various concentrations to the mixed tissue extract and whole intracellular extract described in step 2. Next, an injectable scaffold is prepared (see step 4) or alternatively, a solid scaffold is fabricated (see step 5).

Step 4: Formulating an Injectable Scaffold

The combined mix of extracts generated in step 3 is suspended with a gel compound and formulated into a hydrophilic gel.

Step 5: Fabrication of Transplantable Scaffold Using Electro-Spinning

The combined mix of extracts generated in step 3 is lyophilized in a lyophilizer for 2 days. Then the lyophilized extract is dissolved in 1,1,1,3,3,3 Hexafluoro-2-Propanol (HFP) (Sigma). The Extract solution is left to stir at least 24 hours at room temperature, or in ~50° C. water-bath for overnight before electro-spinning, to ensure complete dissolution. The supernatant is collected for electrospinning.

Fibers are electrospun by using a syringe pump (Fisher) to eject solution from a 3 ml syringe through an 18-gauge needle at a delivery rate of 0.5-1.0 ml/h, an air gap distance of 10-15 cm, and accelerating voltage of 12-20 kV. Fibers are collected onto an aluminum collector. For measurement of fiber diameters, glass coverslips coated with electrospun fibers are mounted onto metal stubs with carbon tape and sputter-coated for 30 sec with platinum and palladium prior to visualization in an environmental scanning electron microscope.

Step 6: Handling and Using the Scaffold for Skin Regeneration

The injectable scaffold formulated into a gel in step 4 can be applied topically on burn wounds or skin ulcers. The scaffold can be applied in any pharmaceutically acceptable form e.g. a gel, a cream, or an ointment.

The transplantable scaffold resulting from step 5 is removed from the sterile washing solution and then gently stretched until it is flat and then placed on a drying platform. Any drying apparatus may be used that is suitable for drying scaffold material. Preferably, however, the scaffold is placed inside a drying bag (Tyvek) and transferred to a freeze-drier. Following drying, the scaffold is stored at above freezing temperature, preferably 0-4° C., sealed in a light-protected environment, at any container suitable for long-term storage. The scaffold, provided as sheet in its dry state is trimmed to a desirable size prior to use. The scaffold then is hydrated with a sterile physiological solution such as sterile 0.9% NaCl solution. Rehydration is done in a dish or preferably while on the surgical site.

The scaffold is used for example to treat skin wounds or skin loss by placing the scaffold directly over the area of the wound or skin loss. Then the scaffold is sutured effectively and covered with sterile wound dressing material.

The invention claimed is:

1. A cell free scaffold having a three dimensional structure and a surface suitable for adherence and proliferation of cells and composed of an extract of cells, wherein the extract consists of extracellular components secreted by, and/or intracellular components extracted from, cells isolated and cultured in vitro, and wherein the scaffold is formulated in injectable form or fabricated in transplantable form, and wherein said scaffold is not fabricated by electroprocessing or electrospinning.

2. The scaffold of claim 1, wherein said extract of cells is prepared from a cell selected from the group consisting of a primary cell and a cell line, and wherein the cell is selected from the group consisting of an animal cell, a mammalian cell, a human cell and a plant cell.

3. The scaffold of claim 1, wherein said scaffold is suitable for administration into a mammal for use in conditions necessitating tissue or organ regeneration, repair or replacement.

4. The scaffold of claim 1, further comprising a scaffold-enhancing agent or an additive.

5. The scaffold of claim 3, wherein said scaffold is seeded with cells that adhere to the scaffold.

6. The scaffold of claim 1, wherein the extract is from cells selected from the group consisting of fibroblasts, keratinocytes, epithelial cells, endothelial cells, embryonic stem cells, somatic cells, pluripotent cells, neural cells, epidermal cells, hematopoietic cells, melanocytes, chondrocytes, hepatocytes, B-cells, T-cells, erythrocytes, macrophages, monocytes, muscle cells, vascular smooth muscle cells, stem cells, differentiated cells, plant cells, mammalian cells, mesenchymal cells, oral and gastrointestinal mucosal epithelia cells, urinary tract epithelia cells, vascular endothelial cells, neural cells, epidermal cells, osteoblasts, intervertebral disc cells, pancreatic cells, angioblasts, bone marrow, mesenchymal cells, myoblasts, cardiomyocytes, amniotic cells, placental cells, genetically engineered cells and combinations thereof.

7. The scaffold of claim 5, wherein the scaffold is redesigned by the adherent cells, and wherein redesigning refers to structural and optionally functional modification of the scaffold by the adherent cells.

8. The scaffold of claim 7, wherein the adherent cells are eliminated from the scaffold.

9. The scaffold of claim 7, wherein the scaffold is structurally modified by at least one cycle of cell seeding and elimination.

10. The scaffold of claim 1, wherein the extract of cells is compartmentalized or fractionated.

11. The scaffold of claim 1, wherein the scaffold is fabricated by a fabrication process selected from the group consisting of solvent-casting and particulate-leaching, gas foaming, fiber meshes/fiber bonding, filament drawing, phase separation, melt molding, compression molding, emulsion freeze drying, solution casting, coating, weaving, and freeze drying.

12. A method of preparing a cell free scaffold having three dimensional structure and a surface suitable for adherence and proliferation of cells for use in conditions necessitating tissue or organ regeneration, repair or replacement, comprising:
(a) isolating cells and culturing said cells in vitro;
(b) preparing a cell extract, wherein the extract consists of extracellular components secreted by, and/or intracellular components extracted from said cultured cells; and
(c) preparing a scaffold from said cell extract, wherein the scaffold is formulated in injectable form or fabricated in transplantable form, and wherein said scaffold is not fabricated by electroprocessing or electro spinning.

13. The method according to claim 12, wherein said cell extract is prepared from a cell selected from the group consisting of: a primary cell and a cell line, and wherein the cell is selected from the group consisting of: an animal cell, a mammalian cell, a human cell and a plant cell.

14. The method according to claim 12, wherein the extracellular components secreted by, and/or intracellular components extracted from said cultured cells are selected from the group consisting of a cytosolic extract, a cytoplasmic extract, a nuclear extract, a whole cell lysate, extracellular extract, and mixtures thereof.

15. The method according to claim 12, wherein said isolated cells are cultured in a cell culture device capable of exerting mechanical forces onto the cultured cells and having a patterned surface.

16. The method according to claim 12, wherein said scaffold is suitable for administration to a mammal for use in conditions necessitating tissue or organ regeneration, repair or replacement.

17. The method according to claim 12, further comprising a scaffold-enhancing agent or an additive.

18. The method according to claim 16, wherein said method further comprises seeding the scaffold with cells that adhere to the scaffold prior to administration.

19. The method according to claim 18, wherein said method further comprises eliminating said seeded cells from the scaffold prior to administration.

20. The method according to claim 19, wherein said scaffold is redesigned by at least one cycle of cell seeding and elimination.

21. The method according to claim 20, wherein said scaffold is seeded with more than one type of cells.

22. A method of providing support to a tissue, or treating conditions necessitating tissue or organ regeneration, repair or replacement in a patient, comprising administering the scaffold of claim 1 in proximity to said tissue.

* * * * *